(12) United States Patent
Whitaker

(10) Patent No.: US 12,263,260 B1
(45) Date of Patent: Apr. 1, 2025

(54) EQUIPMENT DISINFECTION CABINET

(71) Applicant: PURioLABS, LLC, Dallas, TX (US)

(72) Inventor: Mike Whitaker, Plano, TX (US)

( * ) Notice: Subject to any disclaimer, the term of this patent is extended or adjusted under 35 U.S.C. 154(b) by 768 days.

(21) Appl. No.: 17/374,890

(22) Filed: Jul. 13, 2021

Related U.S. Application Data

(60) Provisional application No. 63/051,372, filed on Jul. 13, 2020.

(51) Int. Cl.
*A61L 2/07* (2006.01)
*A61L 2/10* (2006.01)
*A61L 2/24* (2006.01)

(52) U.S. Cl.
CPC ....... *A61L 2/07* (2013.01); *A61L 2/10* (2013.01); *A61L 2/24* (2013.01); *A61L 2202/11* (2013.01); *A61L 2202/121* (2013.01); *A61L 2202/122* (2013.01); *A61L 2202/14* (2013.01); *A61L 2202/15* (2013.01); *A61L 2202/16* (2013.01)

(58) Field of Classification Search
CPC .................................... A61L 2/07; A61L 2/10
See application file for complete search history.

(56) References Cited

U.S. PATENT DOCUMENTS

| | | | |
|---|---|---|---|
| 1,791,736 A | 2/1931 | Mccosh | |
| 3,880,484 A | 4/1975 | Sicina | |
| 4,100,973 A * | 7/1978 | Freudenthal | E21B 7/026 188/170 |
| 4,625,119 A | 11/1986 | Murdock | |
| 4,740,706 A | 4/1988 | Murdock | |
| 5,160,699 A | 11/1992 | Siegal | |
| 5,653,349 A | 8/1997 | Dana et al. | |
| 5,827,487 A | 10/1998 | Holmes | |
| 8,454,901 B1 | 6/2013 | Snyder et al. | |
| 8,584,999 B2 | 11/2013 | Liu et al. | |

(Continued)

FOREIGN PATENT DOCUMENTS

| CN | 111166902 A | 5/2020 |
|---|---|---|
| CN | 211027204 U | 7/2020 |
| CN | 211301256 U | 8/2020 |

OTHER PUBLICATIONS

Condon, "Short on PPE, facilities reuse", Washington Post, Jul. 7, 2020, Section B, p. 1.

(Continued)

*Primary Examiner* — Sean E Conley
(74) *Attorney, Agent, or Firm* — Foley & Lardner LLP

(57) ABSTRACT

A disinfection cabinet can include a transportable cabinet frame having a horizontally disposed base, at least one vertically disposed bounding wall, a horizontally disposed top and at least two access doors mounted to the cabinet frame and providing access to an interior of the cabinet through two separate access door openings. Each of the access door openings can be positioned on an opposite side of the cabinet frame. The cabinet interior can include a rotating framework for holding items for disinfection within the cabinet. The rotating framework rotates about a vertical axis and has plural attachment points. At least two different types of item holders can be configured for attachment to the attachment points. Each type of holder can be configured for holding a different type of item to be disinfected. The cabinet can include at least one disinfecting light source positioned within the cabinet.

20 Claims, 19 Drawing Sheets

(56) References Cited

U.S. PATENT DOCUMENTS

| | | | |
|---|---|---|---|
| 9,162,001 | B2 | 10/2015 | Sunkara et al. |
| 9,433,694 | B1 | 9/2016 | Hsu |
| 9,522,201 | B2 | 12/2016 | Sunkara et al. |
| 10,675,369 | B1 | 6/2020 | Ricciardi et al. |
| 10,716,871 | B1 | 7/2020 | Ricciardi et al. |
| 2003/0160060 | A1 | 8/2003 | Hornblad et al. |
| 2006/0008400 | A1* | 1/2006 | Gutman ............... A23L 3/34 422/292 |
| 2006/0263275 | A1* | 11/2006 | Lobach ............... B01L 1/00 422/186 |
| 2007/0215780 | A1 | 9/2007 | Eichert et al. |
| 2010/0266445 | A1* | 10/2010 | Campagna ........... A61L 2/202 422/23 |
| 2011/0305597 | A1 | 12/2011 | Farren |
| 2012/0153783 | A1* | 6/2012 | Shoenfeld ........... A61L 2/10 362/133 |
| 2013/0256560 | A1 | 10/2013 | Yerby |
| 2014/0061402 | A1 | 3/2014 | Bernstein |
| 2014/0161663 | A1 | 6/2014 | Farren et al. |
| 2016/0008498 | A1* | 1/2016 | Boysset ............... A61L 2/10 422/23 |
| 2017/0095071 | A1 | 4/2017 | Osmond et al. |
| 2018/0030634 | A1* | 2/2018 | Doyle ................... D06F 37/04 |
| 2018/0231176 | A1 | 8/2018 | Sabounjian et al. |
| 2018/0357886 | A1* | 12/2018 | Tavori ................. G16H 40/20 |
| 2019/0314535 | A1 | 10/2019 | Golkowski et al. |
| 2019/0321500 | A1 | 10/2019 | Anderson et al. |
| 2019/0345968 | A1 | 11/2019 | Guilfoyle |
| 2020/0129650 | A1* | 4/2020 | Kim ..................... A62B 25/00 |
| 2021/0299304 | A1 | 9/2021 | Concannon et al. |
| 2022/0031884 | A1 | 2/2022 | Whyte |
| 2022/0062482 | A1 | 3/2022 | Farrell |
| 2022/0175998 | A1 | 6/2022 | Vargas |
| 2022/0265876 | A1 | 8/2022 | Dudycha et al. |
| 2022/0313061 | A1 | 10/2022 | Kim et al. |
| 2022/0313849 | A1 | 10/2022 | Robinson |

OTHER PUBLICATIONS

Steris Corporation; "Pro-Lite Sterilization Tray"; Document #10300689 (Rev A); https://ww1.steris.com/onbDocs/V433/1/928807.pdf; 2017; 2 pages.

Steris Corporation; "Sterile Processing Department: Optimize Your Investment: Pro-Lite Sterilization Trays"; Document #M9278EN. 2019-03, Rev.B; https://ww1.steris.com/onbDocs/V448/0/1864485.pdf; Mar. 2019; 2 pages.

Steris; "Pro-Lite Sterilization Trays"; https://www.steris.com/healthcare/products/v-pro-sterilizers/pro-lite-sterilization-trays; Mar. 1, 2021; 2 pages.

Steris; "SPD and OR Solutions: Driving Innovation. Delivering Throughput"; Document #M4176EN.2021.09 Rev. E; https://ww1.steris.com/onbDocs/V496/0/3762330.pdf; Sep. 2021; 5 pages.

Steris; "Sterile Processing Department: Consumables for V-Pro Low Temperature Sterilization Systems"; Document #M10425EN. 2020-01, Rev. A; https://ww1.steris.com/onbDocs/V468/0/3145489.pdf; Jan. 2020; 6 pages.

* cited by examiner

Fig. 10E

| START | | |
|---|---|---|
| | UV-C | <TIME> |
| | HEAT | <TEMP>, <TIME> |
| | VAPOR | <TIME> |
| | COOL-DOWN | <TEMP>, <TIME> |
| END | | |

Fig. 10F

| SENSOR | CONDITION |
|---|---|
| TEMPERATURE | Controls the heat and cooling cycles |
| HUMIDITY | Controls the vapor, heat and cooling cycles |
| UV-C INTENSITY | Controls the UV-C cycle and bulb status monitor |
| CAROUSEL MOTION | Controls the 360 degree movement status |
| DOOR CLOSED | Controls the safety of enclosure exterior |

Fig. 10G

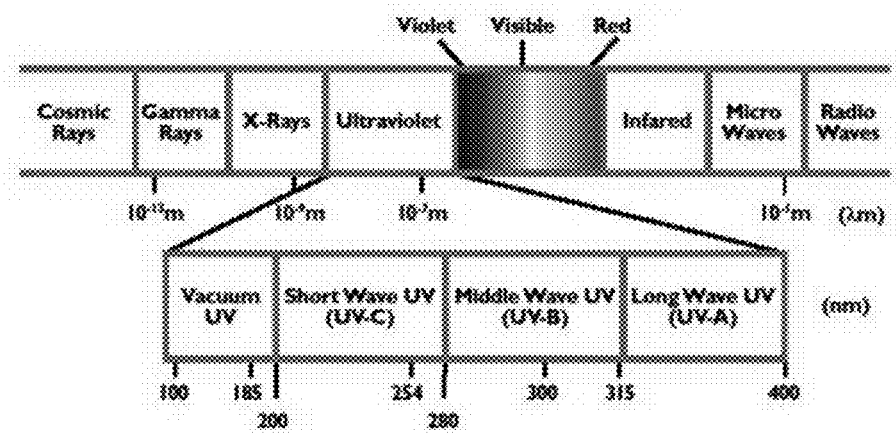

EQUIPMENT DISINFECTION CABINET

RELATED APPLICATIONS

The subject matter of this application is related to U.S. Provisional Application No. 63/051,372, filed on 2020 Jul. 13, which is hereby incorporated by reference in its entirety.

BACKGROUND OF THE INVENTION

Decontamination involves processes or treatments that render devices, instruments, or items and their surfaces safe to handle. Sterilization, disinfection, and antisepsis are all forms of decontamination. Disinfection refers to the elimination of virtually all pathogenic organisms on inanimate objects and surfaces thereby reducing the level of microbial contamination to an acceptably safe level.

The need to disinfect is arguably a more urgent part of our lifestyles today as awareness of our unseen microbial risk has become exponentially greater. Our society may carefully integrate ways to significantly reduce the risk of contaminate transmission between people, animals and objects and surfaces. Governments, institutions, schools, businesses, hospitals, clinics, remote hospitals, ships at sea, casinos, and many other unique environments need to acquire the capability to disinfect the items in use and the current art is extremely limited in the technology, practicality, flexibility and efficiency it offers. In similar historical innovations, institutions installed commercial dishwashers on site as the proven means to disinfect and sanitize eating utensils and dentists and orthodontist offices installed autoclaves on site to disinfect and sterilize dental devices/tools. Those new methods were created and adopted to address the health risks that were known at the time and became the operating standard. With the COVID-19 virus and many other possible contaminants throughout the world, the current art does not have an easily adoptable solution that can help any institution reduce the risk of transmission of potentially fatal viruses or bacteria and other contagions by an improved method for disinfection of items in use.

There is a substantial market and urgent demand for machines and methods of disinfection of many different objects and surfaces that may have come in contact with bacteria, viruses, or other contagions/diseases, collectively referred to as contaminants for this purpose. The market demand centers around the desire to prevent new exposures or additional exposures of these contaminants to people or animals or environments or objects. These contaminants have the common characteristic of being able to harm the health of those exposed. Exposure to contaminants can be fatal.

Humans and animals, when exposed to a contaminant can carry the contaminant and become a transmitter with (symptomatic) and without (a-symptomatic) personal symptoms. Transmission can occur between people or objects or surfaces without the transmitter experiencing the contaminant. Exposure to contaminants can come from unaware transmitters. When a human or animal reports symptoms of exposure to a contaminant, they often seek medical care. They are aware of an abnormality in their health yet are undiagnosed by a formal process and thus, they are a transmitter just before and during their being infected/affected by the contaminant.

For any institutional environment wanting to achieve a lower risk of contamination, definitive measures are required. The health care setting provides the most acute example. Medical patients (human or animals) and the workers who serve them are the most at-risk for contamination due to the worker's frequency and amount of exposures and the existing patient health vulnerabilities. Medical patients enable risk of contamination by submitting to a foreign environment of unknown sterility. Medical workers enable risk to their health by reporting for work duties while also becoming the transmission mechanism patient-to-patient, room-to-room, floor-to-floor, worker-to-worker. Contaminants are invisible and highly transmittable via touch, sneeze, cough, breathing, talking, or any close contact with the contaminant that is then passed along to the next person, object, surface or environment. In any institutional setting (e.g. hospitals, clinics, schools, offices, etc.) organizations spend many billions each year to prevent health consequences of contamination as well as attempt to cure instances of contamination. Objects most commonly contaminated fall into the categories of equipment, devices, and supplies.

Preventive approaches include worker use of disposable products and materials that may come in contact with contaminants and are therefore discarded after one or few uses (e.g.: gloves, masks, face shields, face helmets, testing materials, gowns, slippers, safety glasses/goggles, and more). The current art of disposable products fails when the supply chain fails to supply the demand, leading to shortages and the need to reuse disposable products and add additional risk to workers and customers/patients. The current art does not address the need to reuse disposable items when there are supply shortages. The current art does not make it practical to disinfect and reuse disposable items when it makes sense to do so. For example, a health worker going from room to room in a hospital could reuse certain disposable items if they were disinfected between rooms, or every few hours, or at the end of a work shift, etc.

Preventive approaches include the manual wiping or spraying of surfaces and products and materials that are not disposable include periodic cleaning with user-applied disinfection method (e.g. chemical solutions). Further, preventive approaches include the training of workers on best practices to avoid spreading contaminants as well as applied cleaning methods. The contaminants that remain upon any object or surface following any disinfection effort are directly determined by the thoroughness of the human effort and machine or chemical capability. As contaminants are invisible, the probability of 100% disinfection is very low with the current art as practiced by institutions and the people or animals they serve. As an example in a medical environment, items such as testing equipment, digital thermometers, stethoscopes, blood pressure cuffs, monitoring pads/sensors, clip boards, pens, pencils, digital tablets, worker phones, safety glasses/goggles, worker shoes, durable gloves, and many more items, will come in contact with workers and patients whereby these items are potential transmitters of contaminants and current preventive manual measures are either unavailable or inadequate. In fact, when health care workers are surveyed, they report being scared to go home with their shoes, phone, and other personal effects potentially contaminated. As an example in a school or institution, items such as backpacks, phones, tablets, laptops, lunch boxes, basketballs, footballs, markers, erasers, tape dispensers, staplers, and many more common items will come in contact with workers, guests and students whereby these items are potential transmitters of contaminants and current preventive manual measures are either unavailable or inadequate.

Aside from preventive efforts, governments and institutions spend billions each year on antibiotics and anti-viral drugs administered to human and animal patients after they have been infected due to transmission. If the current art was more effective in preventing transmission, these reactionary expenses could be significantly reduced.

Practicality becomes an important factor in any effort to prevent transmission of contaminants. Since we cannot easily identify transmitters or contaminants, efforts are scrutinized for cost vs. benefit and feasibility. For example, it isn't feasible to disinfect every person, animal, the objects they carry and the clothes they wear upon entry in any doorway. If that were possible, an environment could be made 100% contaminant-free. Per above, people or animals cannot be disinfected in a practical sense. The current art can attempt to isolate if symptomatic but the environment, other people, workers, objects, devices, tools, etc. remain potential transmitters. It is not practical to manually disinfect every inch of surface of every floor, wall, object, device, machine, test material, button, etc. every time it is touched. Because of impracticality of the above, every worker, their equipment, surfaces, objects, devices and anything that could have made contact with a transmitter or contaminant is suspect-which is the primary reason for fear that drives the market demand.

There are many methods that can be used to disinfect objects and surfaces, but the current art has severe limitations. Contaminants can include viruses, bacteria and all contagions. There are many ways to "kill" each of these when encountered on a surface or embedded in material. One proven disinfection method includes the use of ultraviolet light in the "C" classification, UV-C, which operates at light wavelengths 200-280 nm (See FIG. 10G). There are handheld UV-C emitting devices on the market. One handheld product requires a user can use a wand to flash-disinfect a surface. Uneven and inadequate and incomplete exposure to UV-C rays is probable with this type of device. UV-C is a known carcinogen for skin and can damage corneas among other sensitive tissues. For any hand-held solution, the operator is responsible to assure 100% exposure to the needed surface for disinfection and requires the operator to assure the needed exposure time for every amount of surface area, calculated in the art as:

UV dose $\mu Ws/cm^2$=UV intensity $\mu W/cm^2$×exposure time (seconds)

Thus, the proper disinfection "dose" of UV-C light is dependent upon the UV-C light intensity, distance, and exposure time, whereby distance and time are subjective to the user and highly likely to be rushed or skipped as there is no way to see or measure disinfection progress/success (e.g. imagine mowing a lawn and not seeing the cut grass). Also, any blockage of light-of-sight exposure leaves areas unexposed and therefore untreated by this disinfection method.

There are disinfection boxes available on the market whereby consumer users can place their phone, keys, wallet or other small objects inside the container and a dose of UV-C light is introduced. While this box keeps harmful light from reaching outside, objects are placed atop surfaces that fully or partially occlude the light from reaching the objects. The box cannot achieve equal light-of-sight exposure or even assure any light-of-sight exposure based upon the placement of the objects in the container. Adequate exposure is suspect. Timing for what is adequate for the objects and their position within the box to achieve the proper dose is also suspect. Also, these boxes are designed for small objects and their overall design is one for consumer use of personal, small items with extended exposure times required. In general, for containment boxes offering to disinfect objects, there is a high risk of recontamination if the same door and edge outside surfaces are touched after a disinfection effort has been completed on the inside (i.e. "going out thru the in door"). Someone's hand opened the door when contents are suspect and that same hand will open the door to unload disinfected items. The single door approach requires incredible discipline to overcome the recontamination risk.

Another method in the current art involves a large container with a series of holding clips (e.g. the clothesline) strung across many strings or wires and UV-C light bulbs alongside the container walls whereby user(s) can enter the container to attach various items to be disinfected (devices, supplies, masks, shields, gloves, gowns, coats) and then close the container and turn on the UV-C light for 30-180 minutes or more. The limitations to this method are many: The container is too large and heavy to be brought into a normal interior working environment. Contaminated materials/objects may be transported through clean environments to reach the container, exposing additional rooms, floors, HVAC systems, and people to contamination. Items are hung in a way to create uncertain light-of-sight exposure, clips can cover contaminated areas of each item, and the same doors are used to get access to disinfected items as were used to load contaminated items. Additionally, a small "load" is impractical or requires more volume to justify a disinfection cycle due to the size of container or duration of the treatment.

Generally, all forms of the current art for using UV-C light as a disinfection method have the items to be disinfected and the UV-C light bulbs in fixed positions, assuring blind spots for line-of-sight exposure, uneven light dosage, and higher required duration to overcome the above weaknesses, with added sensibility dependency on operators who may not understand how a proper dose of UV-C is administered based upon intensity and distance and time. Additionally, the current art fails to position the items to be disinfected by UV-C light in a manner that exposes all surfaces, leaving pockets of unreachable potential contamination. Also, the current art of using UV-C light as a disinfection method is ineffective upon contaminant bodies that are clumped or intertwined within layers or fibers just underneath the surface.

Another available method of disinfection is to expose the contaminates to high heat, varying levels of humidity, and air flow. High temperatures above 140 degrees Fahrenheit degrade and kill bacteria, viruses and other known pathogens. The current art does not have a practical way of heating surfaces and spaces to achieve disinfection from a portability and containment standpoint. From research, scientists have proven that higher temperatures can destroy living contaminants. Additive to heat is the variable, humidity. Again from research, it is known that high humidity and low humidity have enhanced disinfection effectiveness of living contaminants when combined with high heat. Also from research, it is known that positive air flow (vs. a vacuum) has enhanced disinfection effectiveness upon living contaminants.

Yet another current method of disinfecting items like facemasks or other higher risk items is to contain the items inside large containers and expose them for several hours to vaporized hydrogen peroxide or chlorine-based sanitizing solutions. Liquid compounds when vaporized can reach all exposed surfaces. This approach fails in several ways, including the following. The condensed liquid creates dripping residue from one item to another (following gravity) so that one person's mask residue (for example) drips onto another's. Contaminated items may be transported from a clean space, through clean spaces, to be loaded into a contaminated space. The same doors are used to load contaminated items and their exterior is not disinfected to any known certainty when items are unloaded. The process takes hours to complete and can leave the items moist. User error can result in items stacked to closely to prevent adequate exposure to this disinfection method.

Considering the above described current art of UV-C light exposure, heat and air exposure, and vaporized liquid exposure, each of these approaches fail for certain materials within the items to be disinfected. Not all materials can receive UV-C light, not all materials can withstand high heat, and not all materials can be exposed to hydrogen peroxide, chlorine or many other chemicals that may be used in solution.

The current industry is constantly looking for cheaper, practical, flexible, effective, and portable disinfection products and methods as well as methods and systems for implementation, operating, maintaining, and distribution to the consuming public. Thus, there is a need for a new and improved disinfection product, system, and method of disinfection and general use as disclosed herein.

SUMMARY OF THE INVENTION

The present disclosure relates to medical and personal protective equipment disinfection systems and methods. More particularly, the disclosure relates to a new and improved item disinfection cabinet and method, method for making, distributing, using, and system thereof. Rendering various living contaminants such as viruses and bacteria inert to prevent transmission to other objects and people involves applying a disinfection method to an item. Prior art cases involve a single disinfection method unevenly applied to each item in costly, time-consuming and impractical manners with unknown effectiveness. The disclosed cabinet provides an affordable, convenient, and flexible disinfection method and result. The cabinet includes a portable industrial-grade sealed enclosure for the loading of items needing disinfection with one or more access doors whereby multiple and different disinfection methods are available sequentially or concurrently in a disinfection treatment plan that is selected for its effectiveness per the items and their materials and the targeted contaminants. All disinfection methods are more effective due to the movement between item and disinfection source. Items are presented for treatment via time-saving, quick-change mounting brackets designed purposely to secure and present each item type uniquely. The cabinet enables a room partition separation discipline for "dirty" vs. "clean" item loading and unloading through separate access doors. The cabinet uses computer controlled hardware and software to operate, monitor and set testing and treatment cycles. As such, the general purpose is to provide a new and improved disinfection device and method which has all the advantages of the prior art and none of the disadvantages.

A disinfection treatment plan prescription can be based upon [contaminant×materials×disinfection method×duration].

The current art lacks a comprehensive yet fitting approach to matching the disinfection treatment plan to the items requiring disinfection.

The current art fails to be portable in its use. Requirements of the art include that industrial/institutional disinfection containers may be outside, lifted by forklifts, contaminated products may be transported through clean areas to reach the disinfection location, etc. The disinfection capability of the current art is incapable of being located nearest the sources of contamination to avoid spread of contaminants as well as being operationally practical.

The current art fails to be easily accessible for loading and unloading by the operator whereby operators may physically enter a container to arrange items or may work around hardware, racks, shelves, doors, wires and more to place or remove items. This limitation places significant bending, reaching, and other movements that can create injury over time or are movements not possible for aged or small or large persons.

The current art fails to leave the environment inert following vapor treatments whereby users are cautioned when the enclosure is opened that residue can remain that is hazardous to operators or item users. Additionally, the current art involves external evacuation of air/vapor or open door "airing out" of the enclosure to render the items and enclosure air inert to humans or animals. These provisions are further inflexibility, danger, and cost to the institution.

The current art fails to be time-efficient in its use. Waiting an hour or hours for a process to complete requires significant extra inventory of the items to be disinfected. Waiting until a container is full to run a "cycle" creates unnecessary wait time or requires excess inventory. Transporting disinfected items from a disinfection site to the area of use is time-consuming and laborious.

The current art fails to be affordable in its use. During the COVID-19 epidemic alone, governments and institutions have spent hundreds of millions of dollars on 3rd party sterilization services using the above approaches to disinfection, with expenses as high as $7 per mask disinfection. Affordability is possible when the government or institution can self-administer item disinfection on-demand in a controlled manner. The current art lacks availability for a disinfection solution for common objects that come in contact with contaminants. A school, business, or institution desiring to have a disinfection capability cannot find affordable assets to purchase so that they have such capability in convenient locations when they need it at an operating complexity they can execute with confidence.

The current art lacks a comprehensive approach to matching the disinfection treatment plan to the items requiring disinfection.

The current art lacks the ability to combine two or more disinfection methods in a manner that customizes a disinfection treatment plan (based upon items to be treated or contaminants targeted).

The current art lacks the ability to provide a multi-method attack upon contaminants within the same treatment cycle whereby thoroughness is enhanced by employing multiple disinfection methods simultaneously or in a series within the same cycle.

The current art lacks robustness and discipline whereby the user does not have pre-configured treatment plan options or software controls that are of known efficacy for the varied items and materials and circumstances encountered by the government or institution. Rather, the current art requires the user to manage key aspects of technologies and treatments as a pseudo-expert to assure treatment efficacy without the assistance of technology controls that operate and communicate system and cycle status.

The current art lacks the ability to be a closed system whereby the air and vapor generated for disinfection purposes and fluids can be rendered inert and of nominal impact to operator or item users immediately following treatment. Rather, existing systems require exhausted air, heat, vapor to outdoors which is at either great expense to modify buildings or at great inconvenience as disinfection may be performed outside the normal workspace for the institution.

A disinfection cabinet includes: a transportable cabinet frame having a horizontally disposed base, at least one vertically disposed bounding wall, a horizontally disposed top; at least one rotating framework for holding and presenting items for disinfection within the cabinet, the rotating framework configured to rotate about a vertical axis and having plural attachment points; at least two different types of item holders configured for attachment to the attachment points, each of the two different types of item holders configured for holding a different type of item to be disinfected; and at least one disinfecting light source positioned within the cabinet.

The cabinet can further include: at least one heat source configured to heat the interior of the cabinet; and at least one vapor delivery source configured to deliver a disinfecting vapor within the cabinet. The vapor delivery source can be configured to regulate humidity and chemical saturation level within the cabinet.

The cabinet can further include: at least two access doors mounted to the cabinet frame and providing access to an interior of the cabinet through two separate access door openings, wherein each of the access door openings is positioned on an opposite side of the cabinet frame. The cabinet can further include: at least one means for circulating air in the interior of the cabinet. An air source can be configured to provide a supply of air to or remove air from the interior of the cabinet.

The cabinet can further include: a control system configured to control and regulate application of multiple disinfection methods in accordance with a customizable treatment plan. The customizable treatment plan can be based upon the type or composition of items to be disinfected.

The cabinet can further include: for at least one of the at least one framework, at least one guide feature extending vertically for at least a majority of a height of the framework, the guide feature extending along a parallel to an axis of rotation of the framework so as to nudge items on the rotating carousel into intended positions within a predefined circumference around the axis of rotation as the framework rotates. The framework can include one or more vertically disposed outer members having the one or more attachment points, and wherein at least one item holder attached to one of vertically disposed outer members is positioned with a centerline that is angled between an intersection of a first plane tangent to a circumference of rotation of the vertically disposed outer member and a second plane extending along the axis of rotation of the framework as well as the vertically disposed outer member.

The cabinet can further include: a drive mechanism configured to rotate the rotating framework, wherein the drive mechanism is configured to permit slippage of rotation of the framework in case of blockage or manual movement of the framework during loading or unloading.

A method for disinfecting items includes: opening a first access door providing internal access to a transportable disinfection cabinet through a first opening in the cabinet; loading through the first opening a batch of different items onto at least two different types of item holders, each of the two different types of item holders configured for holding a different type of item to be disinfected, each of the items holders being attached to an attachment point on a rotating framework within the cabinet; closing the first access door after loading the batch of items; causing the cabinet to perform a disinfection process on contents of the cabinet, wherein the disinfection process includes: rotating the framework on a vertical axis of rotation within an interior of the cabinet, and exposing the items to a disinfecting light source positioned within the cabinet; in response to an indication from the cabinet that the disinfection process is complete, opening a second access door providing internal access to the cabinet through a second opening in the cabinet positioned on an opposite side of the cabinet from the first opening; and removing the batch of items from the framework through the second opening.

The disinfection process can further include: exposing the items to air movement and circulation within the cabinet, operating a heat source configured to heat the interior of the cabinet, and operating a vapor delivery source configured to deliver a disinfecting vapor to the interior of the cabinet. The disinfecting vapor can include water vapor, wherein the water vapor raises a humidity level in the cabinet.

The disinfection process can be driven by a control system configured to control and regulate application of multiple disinfection mechanisms in accordance with a customizable treatment plan. The control system can be configured to receive data from one or more sensors within the cabinet to sense: motion of items within the cabinet, and operation of one or more disinfection methods, wherein the control system is configured to control the treatment plan in response to data received from the one or more sensors. The customizable treatment plan can be based upon the type or composition of items to be disinfected.

The method can further include: at least one guide feature of the cabinet nudging items on the rotating carousel into intended positions within a predefined circumference around the axis of rotation as the framework rotates.

The framework can include one or more vertically disposed outer members having the attachment points, and wherein at least one item holder attached to one of vertically disposed outer members is positioned with a centerline that is angled between an intersection of a first plane tangent to a circumference of rotation of the vertically disposed outer member and a second plane extending along the axis of rotation of the framework as well as the vertically disposed outer member. The items can include personal protective equipment.

BRIEF DESCRIPTION OF THE DRAWINGS

FIG. 10E illustrates pre-set or variable treatment plans that are a combination of disinfection methods, either in serial or overlapping order, with adjusted thresholds and duration FIG. 10F illustrates use of sensors to assure the needed environmental factors are reached and maintained to assure treatment efficacy and operator safety.

FIG. 10G illustrates the range of UV light in the electromagnetic spectrum.

DETAILED DESCRIPTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

In the following description, references are made to various embodiments in accordance with which the disclosed subject matter can be practiced. Some embodiments may be described using the expressions one/an/another embodiment or the like, multiple instances of which do not necessarily refer to the same embodiment. Particular features, structures or characteristics associated with such instances can be combined in any suitable manner in various embodiments unless otherwise noted. By way of example, this disclosure may set out a set or list of a number of options or possibilities for an embodiment, and in such case, this disclosure specifically contemplates all clearly feasible combinations and/or permutations of items in the set or list.

Figure 1:
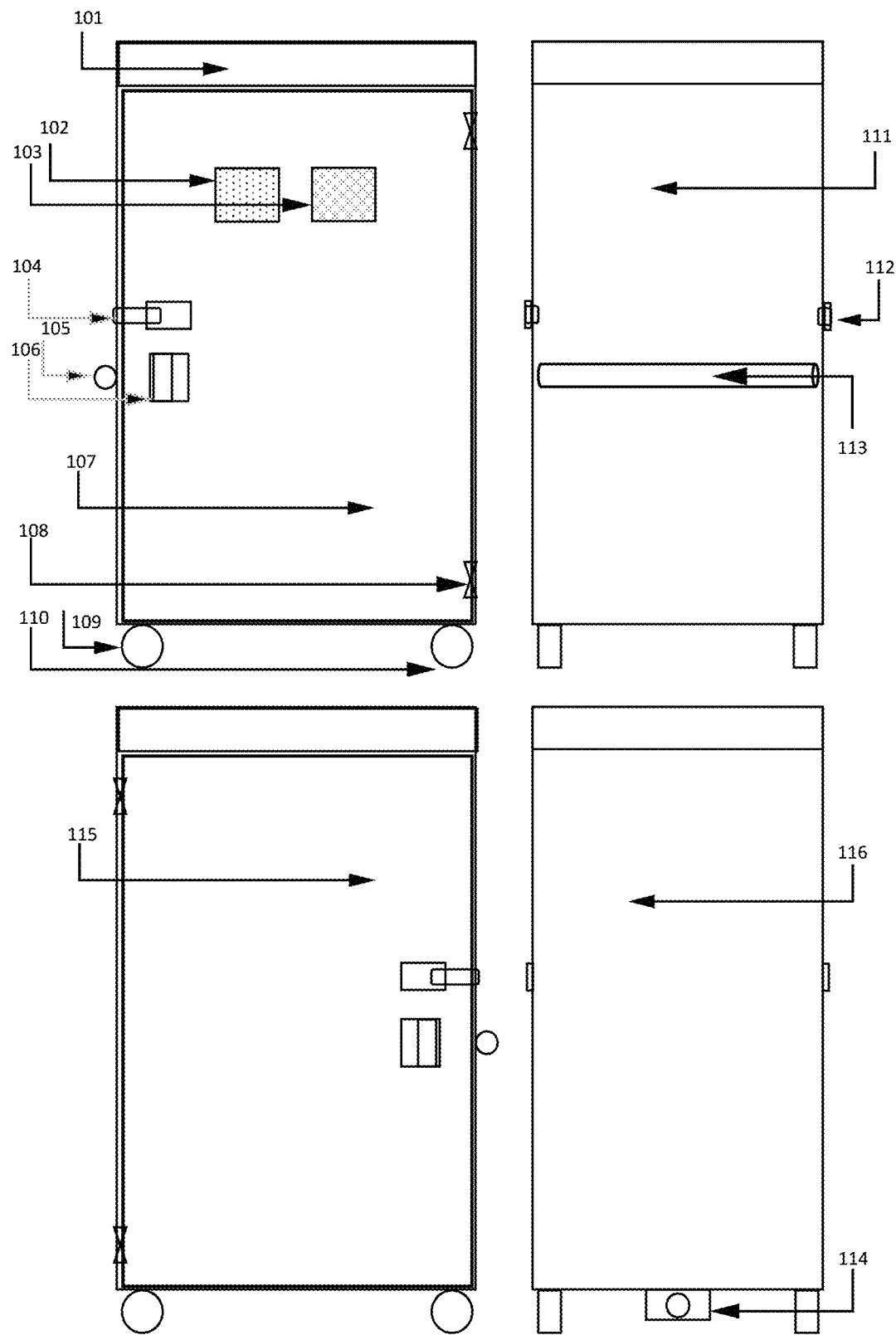
FIG. 1 illustrates a high perspective view of the external surfaces and working components and important features of the cabinet.

FIG. 1 illustrates a view of the external surfaces and working components and important features of a disinfection cabinet. The cabinet contains all electronics and drive and pump and actuating components in the area 101, which can be separate from the interior of the cabinet to protect possible sensitive components from the harshness of disinfection methods, whereby access to area 101 can be via a separate access door from above. For the same purposes, area 101 could be located on any other side of the cabinet. A right side access door 107 the cabinet can include a see-through safety window 102 and operator control panel/screen 103. Alternatively, a see-through window 102 could be located on any surface of the cabinet and operator control panel/screen 103 could be located on any surface of the cabinet. Security latch 104, 112 that applies locked and sealed pressure to the door enclosure can be centrally located along the vertical dimension. One or more security latches can be used for the same purposes. Each access door offers a pull-handle 106, located centrally on the vertical dimension. One or more door handles can be used for door opening. Door hinge 108 allows the door to swing open and contains the wiring necessary for door components whereby the threaded wiring between cabinet and door is not visible to the operator when door is open or closed. One or more door hinges could be utilized in other locations for one or more access doors. For portability ease, the cabinet can incorporate a push/pull handlebar 105, 113 and swivel wheels 109 and fixed wheels 110 to allow a single person to easily maneuver the cabinet and steer from the handle side 111 of the cabinet. Alternatively, one or more handles can be used to grip and maneuver the cabinet and can be located elsewhere on the cabinet exterior. A left side access door 115 can feature components common to the right side access door. The wall-side of the cabinet 116 can be designed to be placed against a wall to allow for a natural separation between operating sides and openings. The cabinet can be configured to have no protruding cords or parts that can catch during transport or operation and power inlet 114 is ready to accept a common 120v power connection and is located where any connected power cord will not interfere with operator movement or create a tripping hazard.

Figure 2:
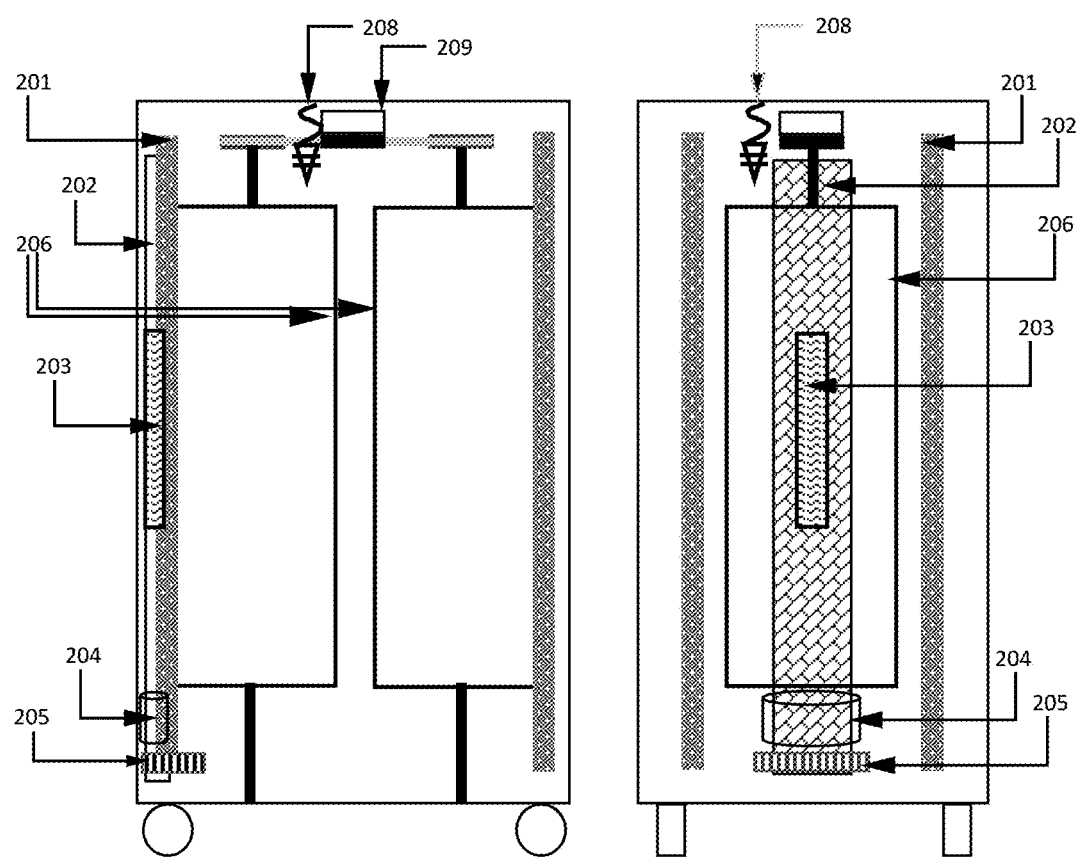
FIG. 2 illustrates a high perspective view of the internal space and working components and item movement and light circulation of the cabinet, including the item movement multi-exposure embodiment.
Figure 2:
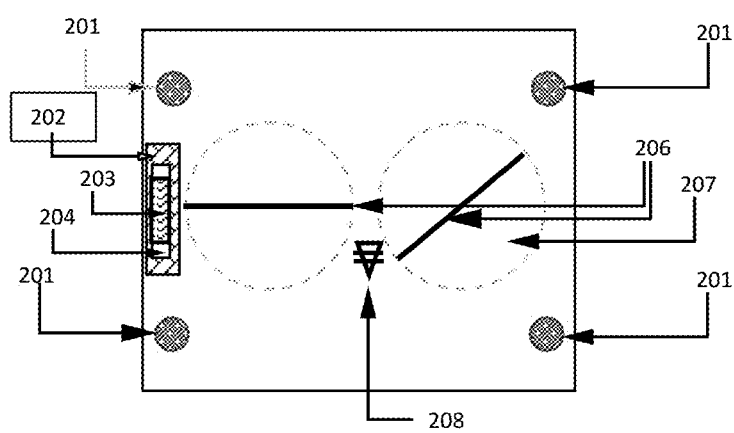

FIG. 2 illustrates a view of the interior surfaces, working components and important features of the cabinet. Disinfection Method 1 (light) can be positioned in a manner that provides multi-bulb and multi-angle access 201. Disinfection Method 2 (heat) can be delivered from heating element 203 and transported by air duct 202. Disinfection Method 3 (air) can be propelled by a fan or blower 204 providing a means for moving air, pushing or pulling air within the enclosure. The fan or blower 204 can move air through a HEPA filter 205 located either interior or exterior of the cabinet. The fan or blower can be located either interior or exterior of the cabinet. Disinfection Method 4 (vapor) can be delivered from a fogging release unit 208 and dispersed throughout the interior via circulating air propelled by fan or blower 204. The delivered vapor can include, for example, hydrogen peroxide, water, solvent, drying agent, fragrance, or a combination thereof. The fogging release unit 208, accordingly can be used to increase the humidity within the cabinet to a desired or target level for disinfection purposes.

The above multiple disinfection methods are part of the simultaneous and serial multi-disinfection method embodiment. The application of the above disinfection methods upon items contained in the cabinet during a treatment cycle has those items transported on or within a framework 206, the item movement multi-exposure embodiment, as one or more frames move on their center points in the complete 360° carrousel movement area 207, driven by power movement 209, providing uniform treatment application. Alternatively, the item could be stationary and the disinfection method can be moved around the item to accomplish the above embodiment. Alternatively, the item can be moved upon a conveyor or carriage for presentation to various disinfection methods. Alternatively, the movement of items can achieve a partial or full exposure of the item as the direction and total movement of the item can be different than above. In the item movement multi-exposure embodiment, due to increased exposure of all facets of an item to various treatments the efficacy of all disinfection methods is enhanced and the time required to achieve a disinfected state is lowered respectively. One embodiment provides a new and improved item disinfection system and method which provides maximum possible item exposure to all disinfection methods and treatments by changing the position between item and disinfection method whereby simultaneous exposure is possible to each item, on all facets/sides of the item (see FIGS. 10A-D).

Figure 3:
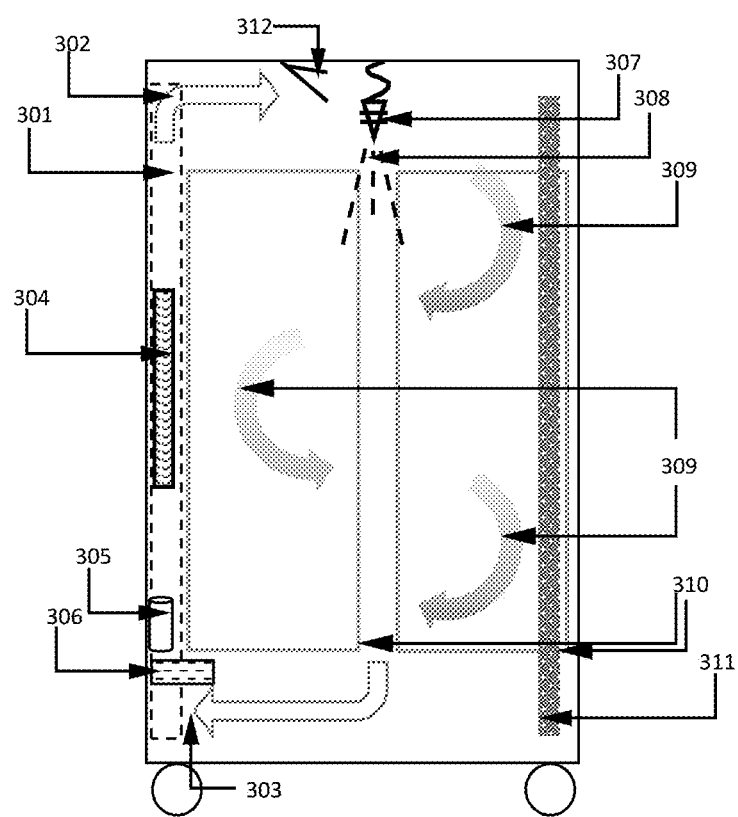
FIG. 3 illustrates a high perspective view of the internal space and the light, air, heat and vapor circulation throughout the cabinet as part of the simultaneous and serial multi-disinfection method embodiment.

FIG. 3 illustrates the simultaneous and serial multi-disinfection method embodiment whereby internal space and the air, heat and vapor circulation throughout the cabinet as air enters the duct 301 at location 303, travels through the air filter 306, through the fan or blower assembly 305, through heating element 304, and exits duct 301 at location 302, and is exposed to one or more light sources 311. Disinfection Method 1 (light 311), Disinfection Method 2 (heat 304), Disinfection Method 3 (air 305) and Disinfection Method 4 (vapor 307, 308) are effective due to enveloping all interior cabinet air and exposed surfaces and materials of items contained in the cabinet during a treatment cycle as the air flow is circulated and tumbled 309 from top to bottom of cabinet as item presentation framework in the form of a carrousel 310 moves the items within the treatment area. Air flow can be guided for balance and best distribution of vapor and air using the air flow guide 312 to selectively deflect portions of the air flow in different directions within the enclosure. The simultaneous and serial multi-disinfection method embodiment can offer two or more disinfection methods that can include ultra-violet light, heating, cooling, air pressure, air movement, and vaporized liquids with or without chemical components, laser light, and more-all of which can be customized as part of any treatment plan based upon the items and materials to be disinfected. The amount, level, intensity, saturation, duration of any disinfection method is adjustable as needed for maximum efficacy of any treatment of any item. The above embodiments can achieve a closed system of air and item movement whereby no air is added or subtracted from the enclosure and requiring no external vents outside the enclosure. Alternatively, the above embodiments can be operated similarly if the fan or blower 204 is moving air sourced from outside the enclosure into the enclosure and moving the air in the enclosure outside the enclosure.

One embodiment provides a new and improved item disinfection system and method which can combine two or more disinfection methods in a manner that customizes a disinfection treatment plan (based upon items to be treated or contaminants targeted) and executes that plan via controls of the hardware. The objective involves a multi-method attack upon contaminants within the same treatment cycle whereby thoroughness is enhanced by employing multiple disinfection methods simultaneously or in a series within the same cycle. For example, sensitive electronic devices may be treated with UV-C and Heat but no Vapor. In another example, sensitive plastic materials may be treated with UV-C and Vapor but no Heat. Additionally, the duration of any disinfection method is part of customized disinfection treatment plan. For example, some materials cannot tolerate long UV-C exposure and so the duration of UV-C can be shortened and other disinfection methods extended.

Figure 4:
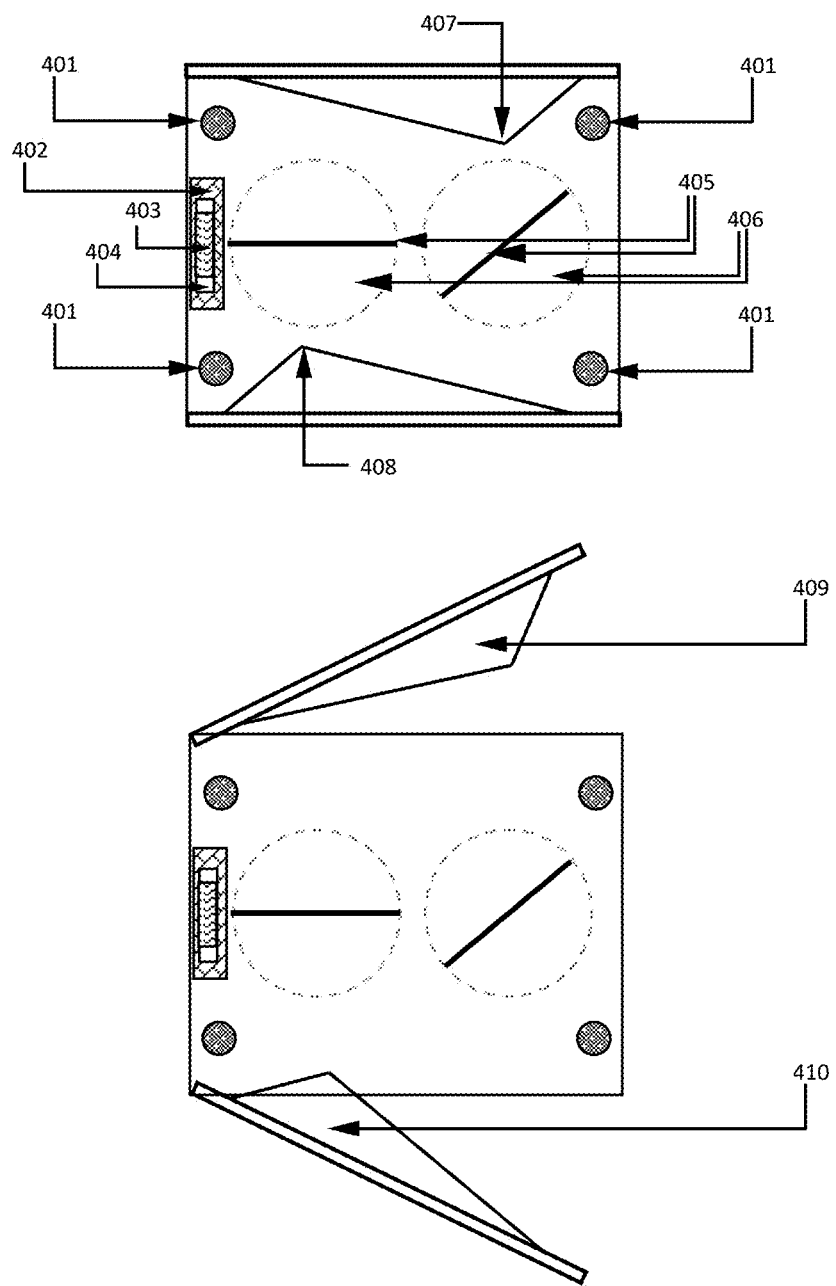
FIG. 4 illustrates a high perspective view of the internal space and the cabinet's item physical guide embodiment and interior space saving embodiment.

FIG. 4 illustrates the cabinet's internal space using item physical guides to save interior space in accordance with one embodiment. Disinfection Method 1 (light) can be positioned in a manner that provides multi-bulb and multi-angle access 401. Disinfection Method 2 (heat) can be delivered from heating element 403 and transported by air duct 402. Disinfection Method 3 (air) can be propelled by a fan or blower 404 providing a means for moving air, pushing or pulling air within the enclosure. As the framework carrousels 405 move at their center point 360° within carrousel movement area 406, items contained within the carrousel could potentially shift whereby all or a portion of any item could extend beyond the carrousel movement area 406 and if so, item physical guide point 407, 408 is positioned to nudge the item toward carrousel movement area 406 and preventing the item from leaving the carrousel movement area 406 where the item would be prevented from receiving or would prevent other items from receiving full treatment by chosen disinfection methods. The triangular form 409, 410 on the interior of the cabinet provides the physical guide points 407, 408 and the triangular form 409, 410 occupies significant interior area that would otherwise be open and require more disinfection efforts if triangular forms 409, 410 did not exist. Physical guide points could protrude from another interior surface of the cabinet to correct the position of any item as a means to the item physical guide embodiment. Interior panels could protrude from one or more surfaces to occupy space as a means to the interior space saving embodiment. The item physical guides provide a new and improved item disinfection system and method which has built-in physical guide material on the interior of the enclosure or door assembly whereby any item that becomes misaligned with its intended position as it rotates is nudged toward its original intended position so that it remains in place for exposure as well as it does not affect any other item or the cabinet's mechanisms. Alternatively, the item can be moved upon a conveyor or carriage and a similar physical guide can be positioned to assure the item remains in its intended position throughout the treatment cycle.

Figure 5:
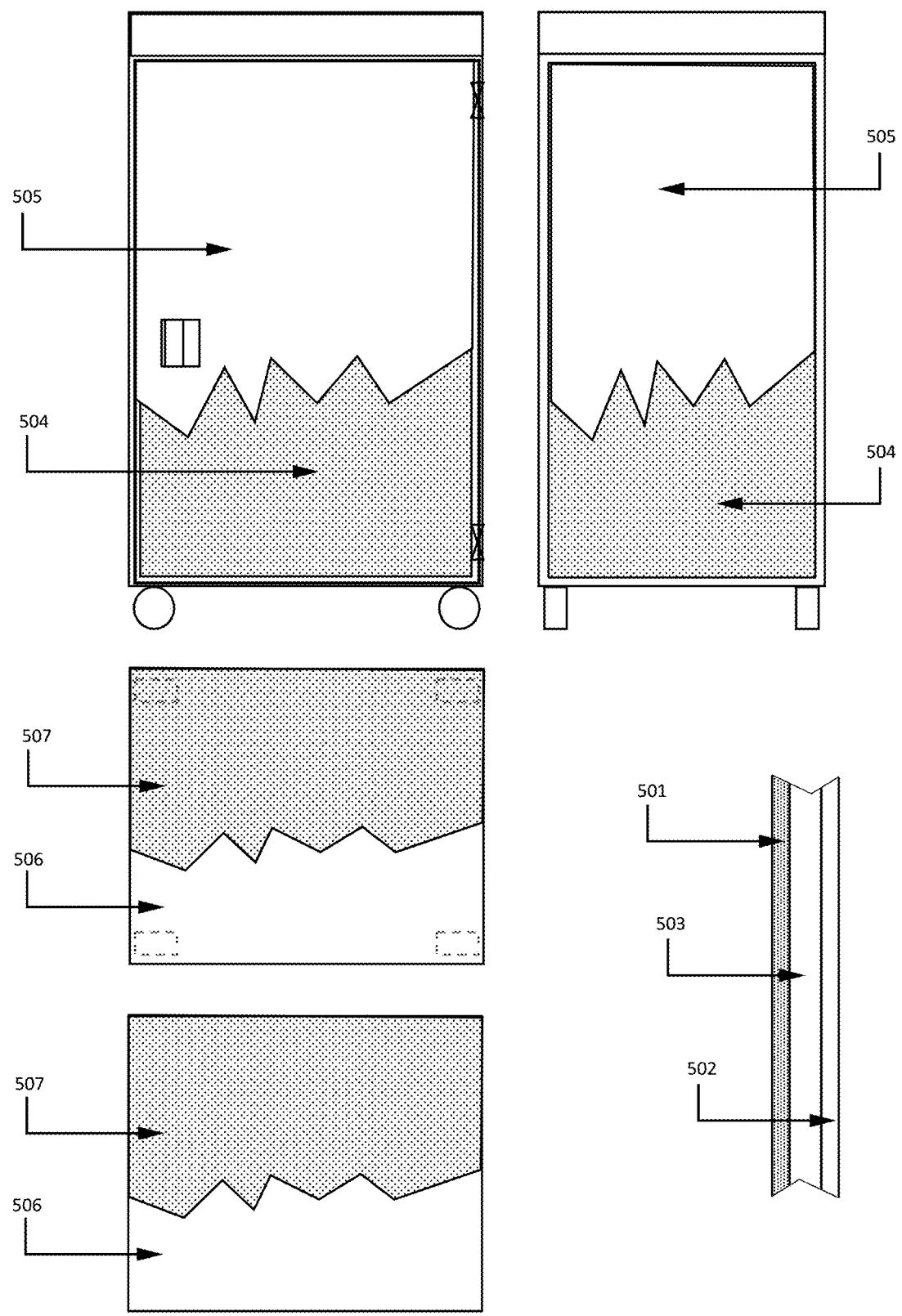
FIG. 5 illustrates a high perspective view of the cabinet's multi-layered frame whereby all facets of the cabinet have at least two layers and a space between those layers, allowing for all wiring and connectivity to be embedded between those layers and also providing insulation and heat dissipation between the interior and exterior of the cabinet.

FIG. 5 illustrates a multi-layered frame whereby any or all facets of the cabinet can have at least two layers, inner layer 501, outer layer 502, and a space between those layers 503, allowing for all wiring and connectivity to be embedded between those layers and also providing insulation and heat dissipation between the interior and exterior of the cabinet. In one embodiment, all sides of the cabinet have inner layer 504 and outer layer 505 and the top and bottom sides of the cabinet have inner layer 507 and outer layer 506.

Figure 6:
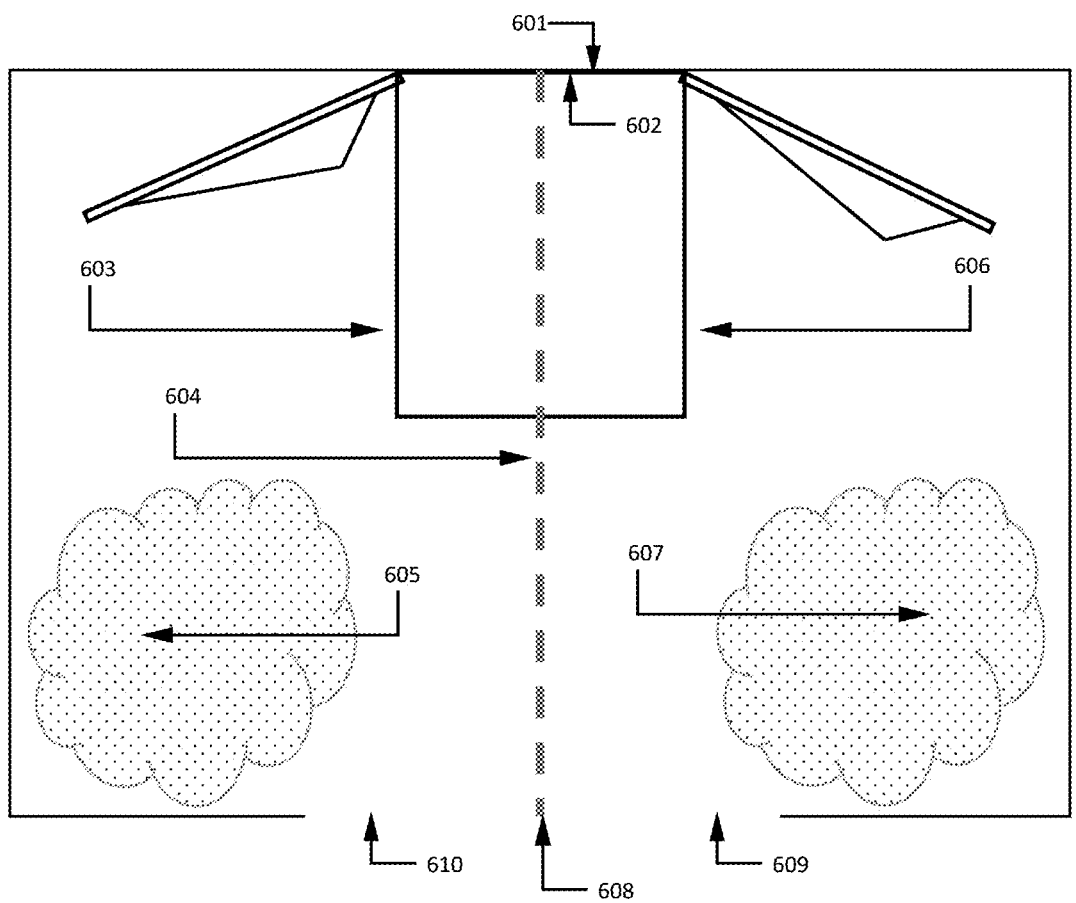
FIG. 6 illustrates a high perspective view of the cabinet as part of the room partition embodiment whereby the cabinet's multiple doors and cabinet combined with a drape or curtain or wall allows for separate work spaces, one for contaminated and one for disinfected.

FIG. 6 illustrates the cabinet positioned as part of a room partition where a side of the cabinet 602 is placed against a wall 601 with operator loading side 606 opposite non-operator unloading side 603, separated by a temporary or fixed partition or wall 608, allowing for separated work areas, "dirty" loading area 607, "clean" unloading area 605, separated loading doorway from unloading doorway 609 from unloading entrance 610. An operator can organize the inbound and outbound items for treatment based upon the ability for the cabinet and its design elements to be part of the room partition embodiment. Alternatively, the "dirty" loading vs. "clean" unloading access doors and their associated loading/unloading areas could be located differently than illustrated. Alternatively, the cabinet can be positioned to be part of a room partition in the middle, left or right location, as part of the room partition embodiment. This embodiment essentially includes a new and improved physical discipline in the disinfection process whereby the cabinet can have more than one access door, one or more doors for "dirty" items and one or more doors for "clean" items, allowing the operator to partition their cycle schedule and loading/unloading discipline with re-contamination risk lowered extensively. The embodiment allows for a 1st operator and 2nd operator, each operator working on separate side of the cabinet so a physical barrier 604 can be erected around the cabinet (e.g., drape) so that the room is separated in half, dirty vs. clean (see FIG. 6).

Figure 7:
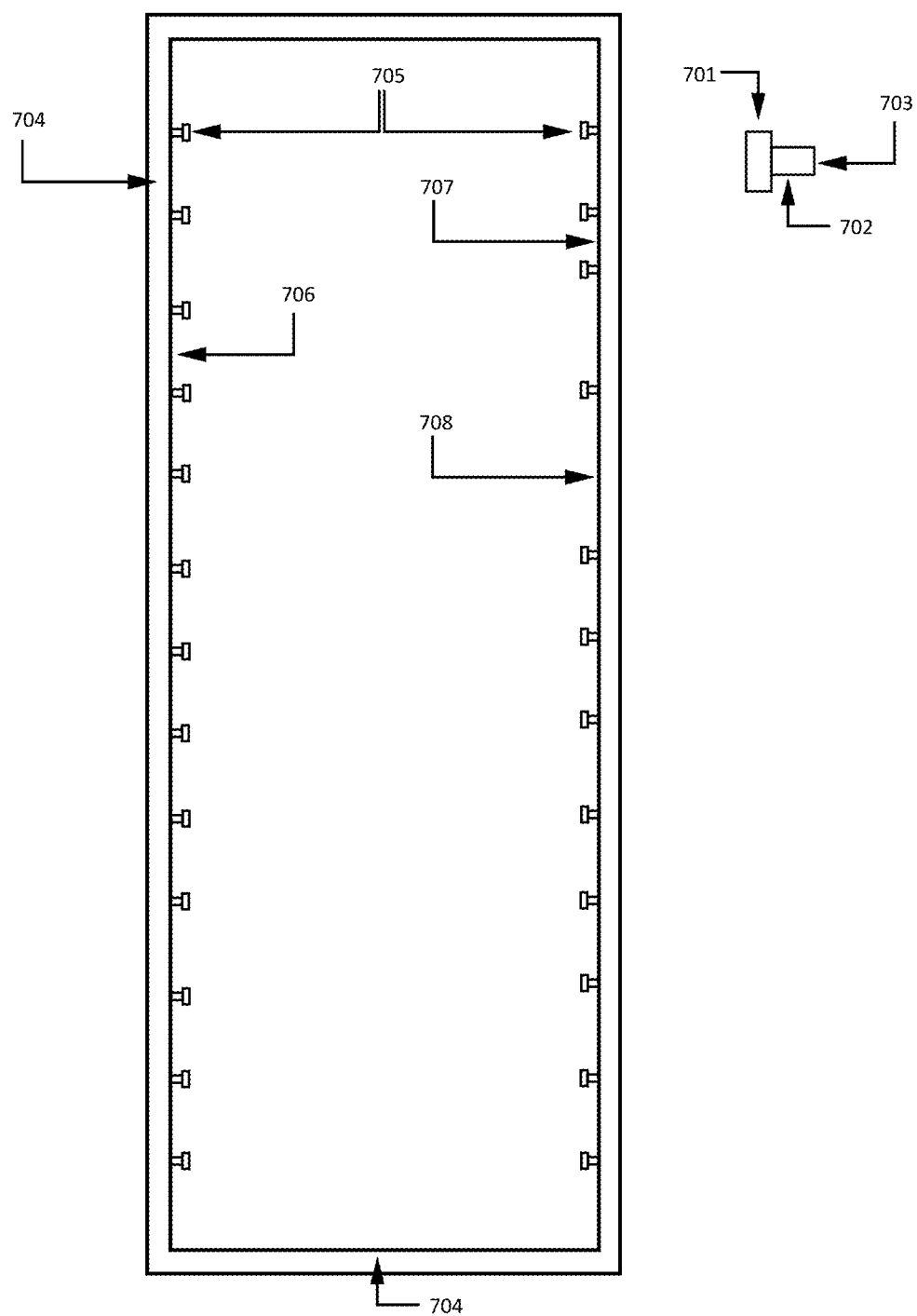
FIG. 7 illustrates a high perspective view of the item presentation framework embodiment of the cabinet whereby item mounting attachment points are located on the framework and item mounting brackets can be attached at one or more item mounting attachment points.

FIG. 7 illustrates the item presentation framework and attachment embodiment of the cabinet whereby item mounting attachment points 705 are located on the framework 704 in accordance with one embodiment. Item mounting attachment points can be constructed of an edge 703 adjacent to the framework 704, an extension 702 from the framework that attaches to an anchoring point 701 whereby the anchoring point 701 has a physical attribute that provides anchoring leverage for any object with a reciprocating receiving attribute. Item mounting attachment points 705 can be spaced 706, 707, 708 along the framework or surface plane of the item presentation framework in an arrangement that provides flexible placement of item mounting attachments or the items themselves. Alternatively, the item presentation framework could be a different shape or dimensions while accomplishing the same mounting result for item mounting attachments, as an example, the item presentation framework could be a cylinder and item mounting attachment points can be holes and/or pegs positioned on and/or throughout the surface of the cylinder and selective physical guides can maintain the item's intended position. Alternatively, item mounting attachment points can be achieved for attachment using different attachment methods, including clips, magnets, brackets, notches, and any other means of attaching an item or item mounting bracket to the item presentation framework. The item presentation framework and attachment embodiment enables rapid loading and unloading of items within the enclosure via quick-connect item mounting adapters attached to the framework. Unique mounting adapters are provided as part of one embodiment to easily fit specific categories of items without any adaptation or tie-downs or added fixtures, saving the operator loading and unloading time and allowing for a custom mix of items per the needs of the operator. Improved treatment efficacy can be achieved via the item mounting adapters as they are customized to serve each category of item and achieve maximum surface area presentation from all sides of the item which therefore achieves maximum treatment exposure on all sides of the item, thereby lowering cycle times and increasing treatment effectiveness. The movement method and the power applied to the carrousel host framework can allow for 100% slippage if movement is blocked or if manual movement is desired by the operator when loading the enclosure and the carrousel assembly may be rotated to face the operator for loading and unloading purposes.

Figure 8:
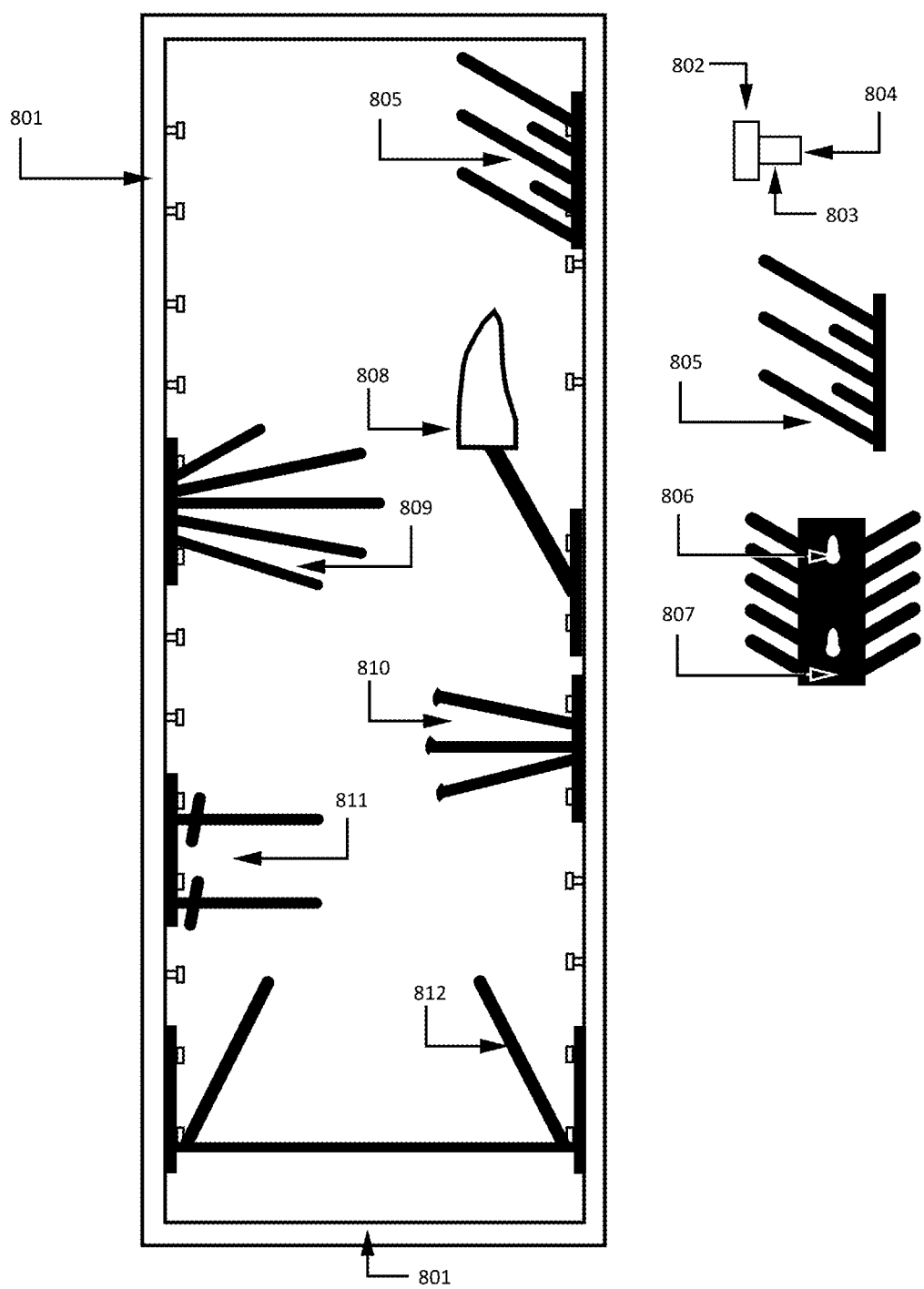
FIG. 8 illustrates a high perspective view of the many possible item mounting brackets variably arranged and attached to the framework as item presentation framework embodiment of the cabinet.
Figure 8:
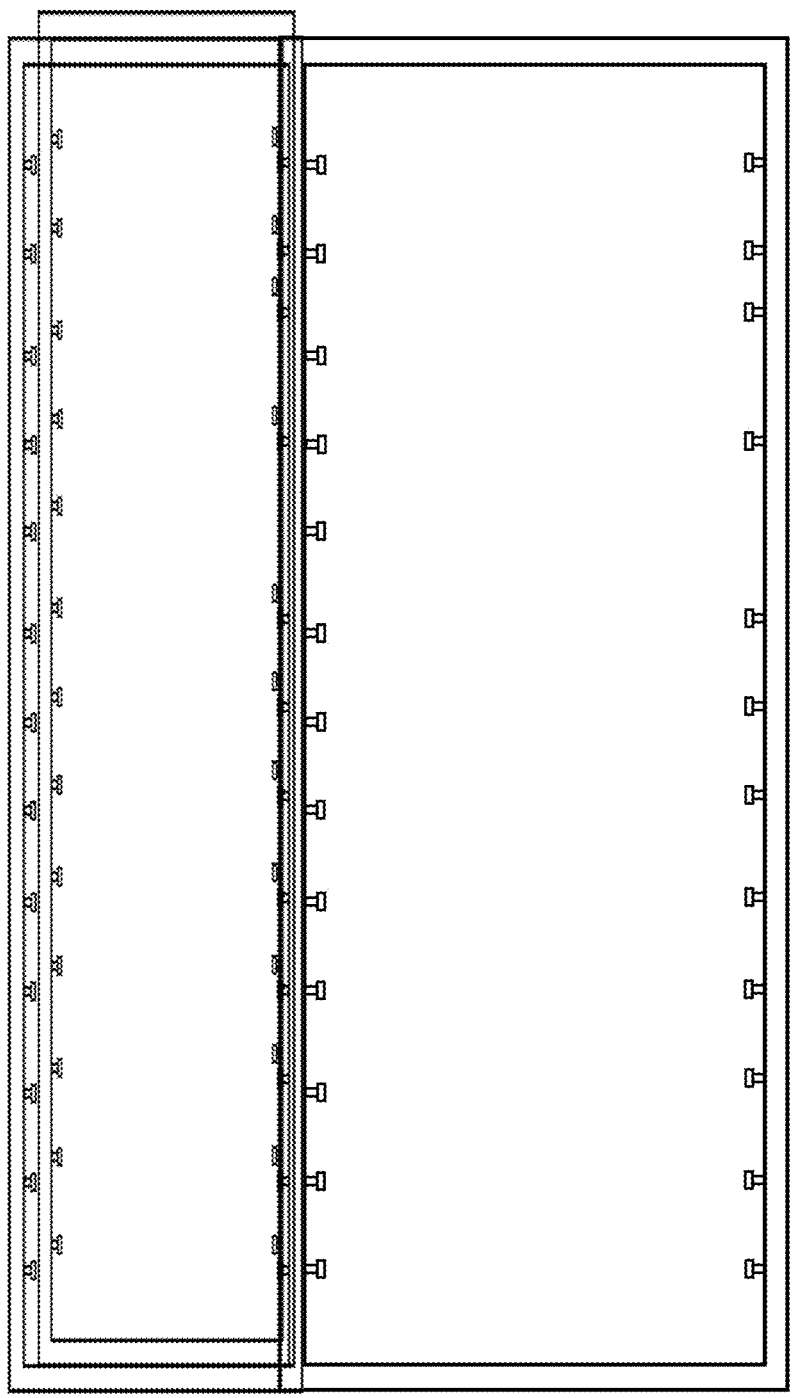

FIG. 8 illustrates possible item mounting brackets that can be used with an item presentation framework, variably arranged and attached to the item presentation framework 801 with the item mounting attachment points 802, 803, 804 as located variably throughout the framework. Item mounting attachments are specifically designed for specific items found in the institution work or user environment, such as face shields 812, eyeglasses or goggles 811, paper or cloth facemasks 810, gloves 809, shoes 808, phone, wallet, keys, rings 805 and more. For any item mounting bracket embodiment 805, the item mounting bracket can use one or more attachment methods or apertures 806 located within a mounting base 807 whereby the item mounting bracket slides or snaps or affixes or attaches to the item presentation framework. The attachment method can protrude from the item presentation framework or the attachment method can protrude from the item mounting bracket, creating an attachment point between framework and bracket. One embodiment provides a new and improved item disinfection system and method which employs an item hosting framework with convenient "quick change" item adapter system via universal attachment points so various item adapters can be employed for the desired disinfection contents within a cycle. The operator of the cabinet may wish to employ a mix of item adapters for a variety of items encountered or a concentration of a specific item mounting adapters can be attached to the hosting framework (e.g. a batch of masks and face shields). One embodiment provides a new and improved item disinfection system and method which employs the "quick change" item adapter system via universal attachment points whereby the item adapters quickly snap into place and have a small protruding locking pin mechanism to prevent unintentional detachment.

Figure 9:
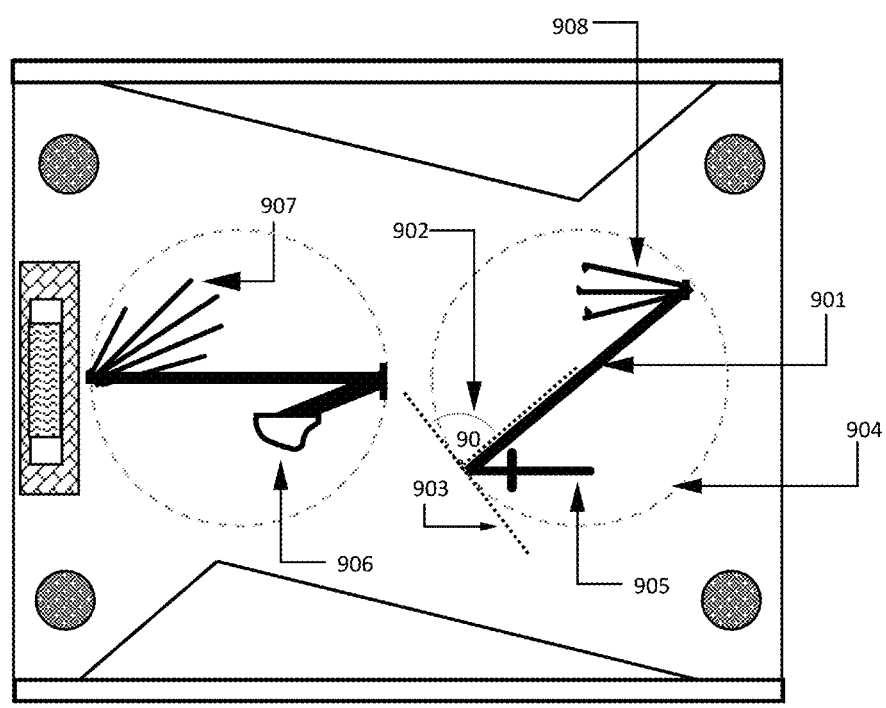
FIG. 9 illustrates a high perspective view of the internal space and item presentation to disinfection methods using the mounting bracket offset embodiment of the cabinet.

FIG. 9 illustrates the internal cabinet space and item presentation to all disinfection methods using an offset mounting bracket whereby the item presentation framework 901 moves within the carrousel movement area 904 and one or more item mounting attachments 905, 906, 907, 908 are attached to the item presentation framework 901. The attachment can be mounted with its centerline at an interior "offset angle" between 0° and 90° from parallel to the item presentation framework (shown as angle 902). The attachment can alternatively be mounted at an angle between 0° and 90° from a perpendicular line 903 whereby the item mounting attachments remain inside the carrousel movement area 904 yet are faced openly at an offset angle. When offset, items opposite each other on the item presentation framework are presented in opposing offset angles so that they do obscure any disinfection method presentation and do not physically collide when mounted and dismounted. This can make mounting and dismounting items easier in and around the item presentation framework such that mounting or dismounting an item doesn't disturb another adjacent item. To further illustrate, within any framework or base of attachment, items mounted directly adjacent or directly opposed will force contact with one another during the mounting or dismounting effort, causing items to unintendedly touch or dismount or displace. One embodiment minimizes the opportunity for items to occlude, touch or displace each other at any time.

Further disclosed herein is an item disinfection system and methods for making, distributing, and using the system with further embodiments.

In accordance with one embodiment, a cabinet can include a new and improved physical enclosure which is portable by one person, can be powered by a single conventional wall outlet or equivalent, self-contained as a closed system, can be operated indoors, can be operated with average personnel with little training, is quiet in operation, and has easy operator access to the enclosure interior.

In one embodiment, sensors, software and lights and screen displays serve as the control mechanisms of one embodiment to allow the operator to use, monitor, and troubleshoot the cabinet thereby assuring a safe and effective execution of the selected disinfection treatment plan.

In one embodiment, the system can be of a durable and reliable construction and may be easily and efficiently manufactured and marketed.

In one embodiment, the system can be made portable so that it can be located nearest the source of contaminants, can be optionally movable by only one person, can be configured to fit through any standard doorway, can be configured to be rolled upon wheels for easier transport, and can be configured to weigh less than 250 pounds.

One embodiment provides a new and improved item disinfection system and method which is constructed of high-grade institution-grade materials such as stainless steel, has no exposed wires, with all drive and control components located outside the disinfection area but located within the cabinet container.

One embodiment provides a new and improved item disinfection system and method which is efficient in the labor required to transport, load, and unload items for treatment as well as efficient in the time required to complete a treatment plan/cycle (generally in 15 minutes or less).

One embodiment provides a new and improved item disinfection system and method whereby the cabinet's software controls indicate the system's status whereby the operator can easily understand the status as "dirty/ready for cycle", "clean/ready to unload" with safety monitoring and messaging if a door is opened prematurely, the "dirty" door is opened before the "clean" door post-cycle, or if both "dirty" and "clean" doors are opened at the same time (these are contaminating events).

Figure 10A:
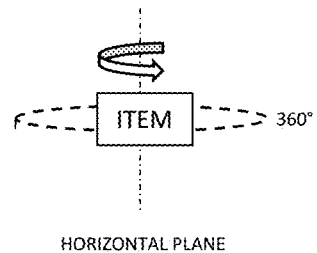
FIGS. 10A-D illustrate exposure to all disinfection methods and treatments by changing the position between item and disinfection method.
Figure 10B:
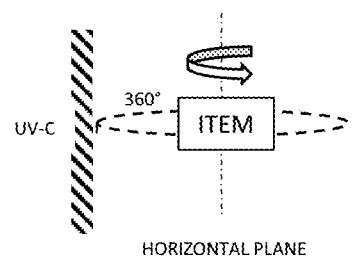
Figure 10C:
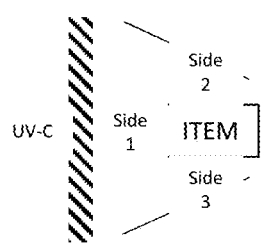
Figure 10D:
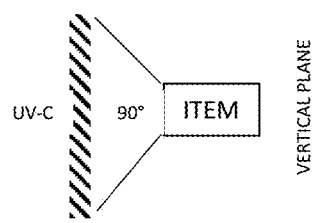

One embodiment provides a new and improved item disinfection system and method which provides 100% light-of-sight UV-C exposure by utilizing one or more UV-C sources whereby we position the item and light exposure to achieve via the item or treatment movement embodiment a 360 degree exposure on the horizontal plane that accomplishes a full exposure to all sides and surfaces of the item within a full range of movement (see FIGS. 10b, 10c).

One embodiment provides a new and improved item disinfection system and method which provides UV-C disinfection method from broad angles with a light-of-sight angle not less than 90 degrees up to 180 degrees in the vertical plane for any point of exposure facing the UV-C source, irrespective of item position within the enclosure. Further, this item presentation to the light achieves UV-C exposure to not less than 3 sides/surfaces of the item in the same instance (see FIG. 10D).

One embodiment provides a new and improved item disinfection system and method which provides a heat disinfection method whereby varying temperatures are achieve inside the enclosure for various durations to render various living contaminants inert or dead. The cabinet monitors interior temperatures to achieve a known surface temperature of the exposed items. Based upon item material sensitivities, the temperature may be increased and time decreased or temperature may be decreased and duration increased. The cabinet can reach temperatures up to 160° F. within 40 minutes or less. The addition of the rotating carrousel embodiment makes distribution of heat treatments among all items very uniform.

One embodiment provides a new and improved item disinfection system and method which provides air pressure and air flow disinfection enhancement method whereby the cabinet will maximize air pressure within the enclosure in order to increase the harshness of the environment upon living contaminants. The addition of the heat embodiment makes internal air especially effective in disinfection. The addition of the rotating carrousel embodiment makes distribution of air among all items very uniform.

One embodiment provides a new and improved item disinfection system and method which introduces and circulates a vaporized fog throughout the interior enclosure, coating all surfaces of contained items for the purpose of disinfection or freshening of appearance or smell. The amount of vaporized liquid and duration of application is controlled per the treatment plan. The liquid is a water-based chemical solution. The addition of the rotating carrousel embodiment makes distribution of vapor treatments among all items very uniform.

One embodiment provides a new and improved item disinfection system and method which provides humidity disinfection enhancement method whereby the cabinet's liquid vaporization capability will increase humidity within the enclosure in order increase the harshness of the environment upon living contaminants more sensitive to heat+humidity combination. The cabinet can have the ability to apply heat+air flow+low humidity combination for maximum disinfection of one category of contaminants while separately applying heat+air flow+high humidity combination for maximum disinfection of another category of contaminants. The addition of the rotating carrousel embodiment makes distribution of heat and air and humidity treatments among all items very uniform.

One embodiment provides a new and improved item disinfection system and method which provides air flow drying enhancement method whereby the cabinet will move high volume of air across the surface of all contained items to facilitate drying of moist items and surfaces. The addition of the heat embodiment makes air more effective in moisture evaporation from item surfaces. The addition of the rotating carrousel embodiment makes distribution of air among all items very uniform.

One embodiment provides a new and improved disinfection system and method which allows pre-set or variable treatment plans that are a combination of disinfection methods, either in serial or overlapping order, with adjusted thresholds and duration (see FIG. 10E).

One embodiment provides a new and improved item disinfection system and method which has multiple sensors that serve to control the operating environment before, during, and following a treatment cycle. Use of these sensors assures the needed environmental factors are reached and maintained to assure treatment efficacy and operator safety. If any sensor indicates an incorrect status or no status, the system will not operate (see FIG. 10F).

Figure 11:
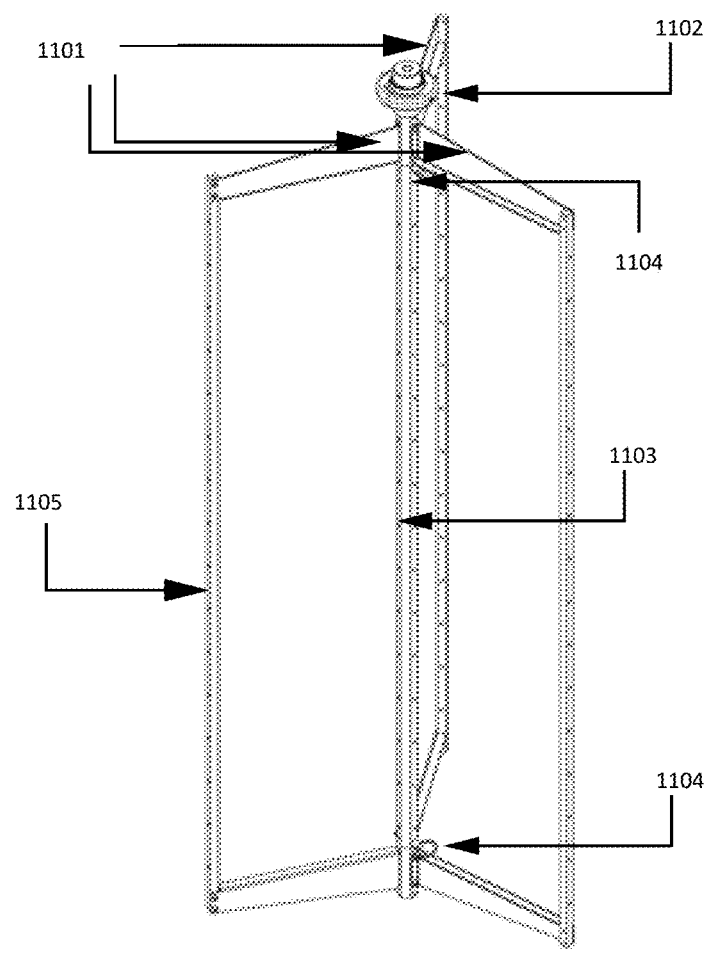
FIG. 11 illustrates a multi-wing carrousel embodiment whereby the carrousel is driven from the drive clutch.

FIG. 11 illustrates a multi-wing carrousel embodiment whereby the carrousel is driven from the drive clutch 102 that rotates the carrousel and allows for adjustable safety slippage, multiple wings 1101 connect to wing frames 1105 that provide maximum use of interior cabinet space around the center shaft 1103 which is removable to create a large interior carrousel space by removing the latch rings 1104.

Figure 12:
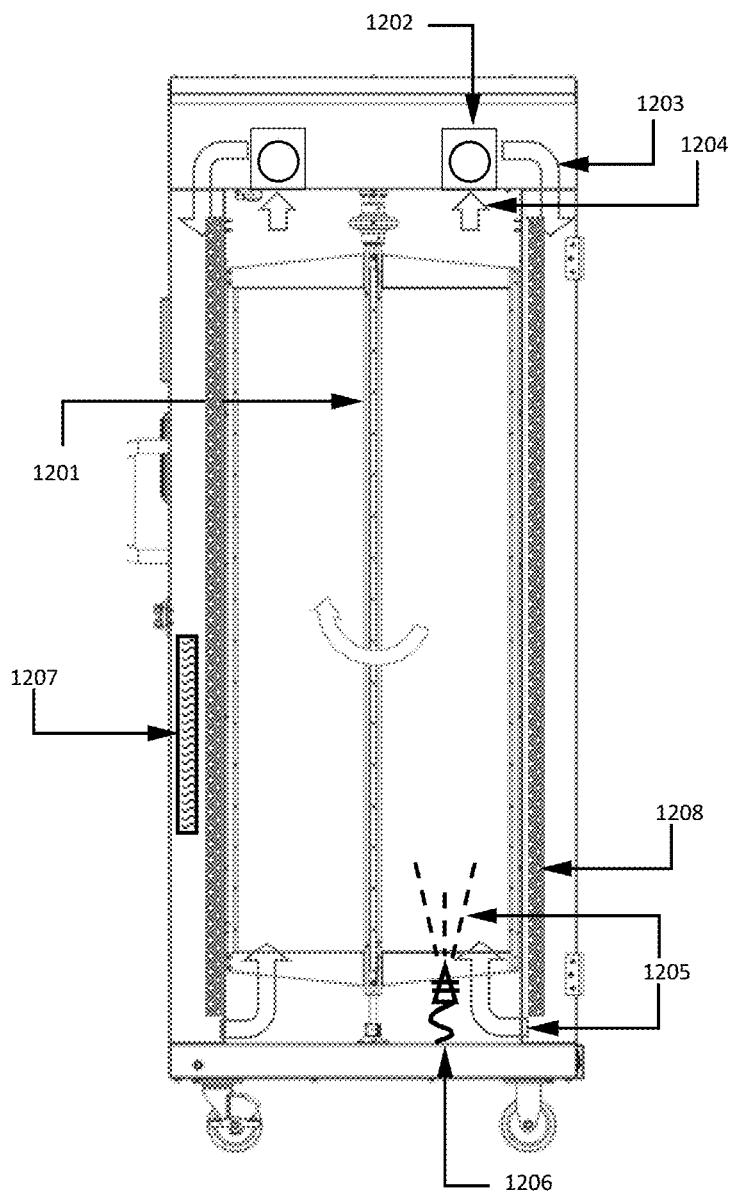
FIG. 12 illustrates a cross sectional elevation view of a four-corner embodiment where the rotating carrousel is surrounded by germicidal light sources.

FIG. 12 illustrates a cross sectional elevation view of a four-corner embodiment where the rotating carrousel 1201 is surrounded by germicidal light sources 1208 as interior air is ingested 1204 into a fan 1202 outside the interior space and air is moved into the nearest corner duct 1203 moving downward to the cabinet bottom, passing by heater 1207 and re-entering the cabinet 1205 whereby the air can force interior microbes and vapor 1206 vertically while the carrousel is moving items horizontally. The resulting air flow

1205 1204 passes all along the warm surface of the germicidal light component 1208, providing a cooling effect upon the light.

Figure 13:
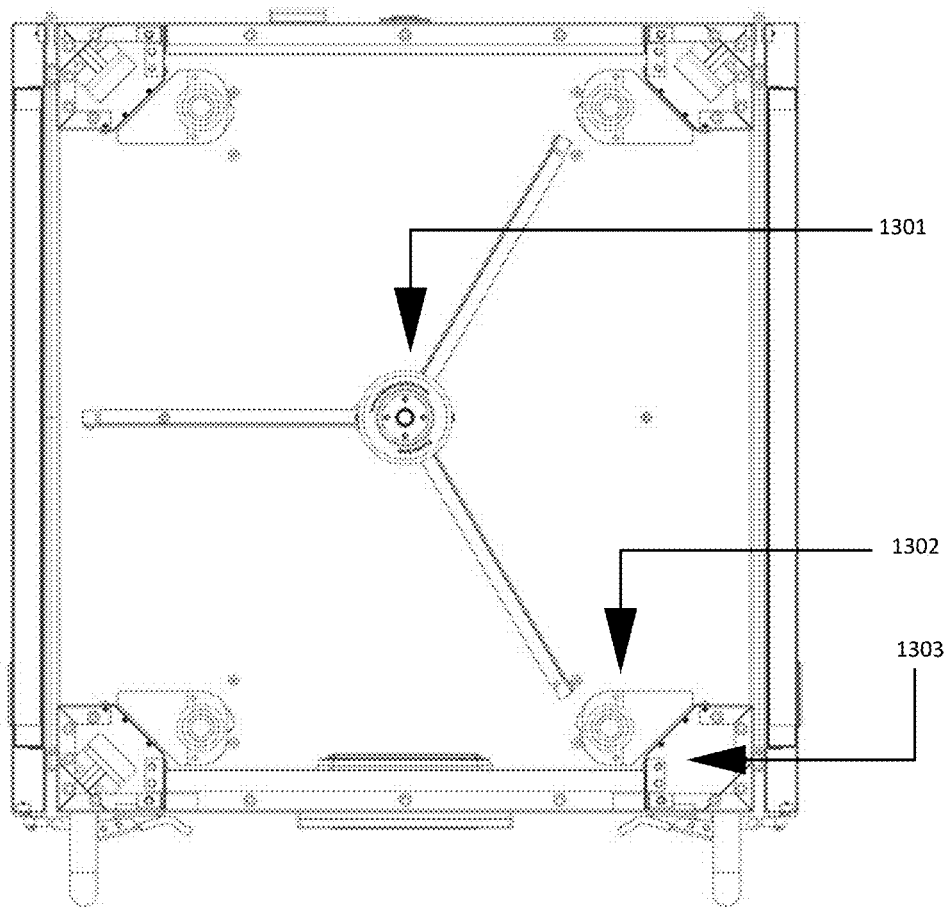
FIG. 13 illustrates a cross sectional overhead view of a four-corner embodiment where the rotating carrousel is surrounded by germicidal light sources.

FIG. 13 illustrates a cross sectional overhead view of a four-corner embodiment where the rotating carrousel 1301 is surrounded by germicidal light sources 1302 as interior air is moved into the nearest corner duct 1303 moving downward to the cabinet bottom.

Figure 14:
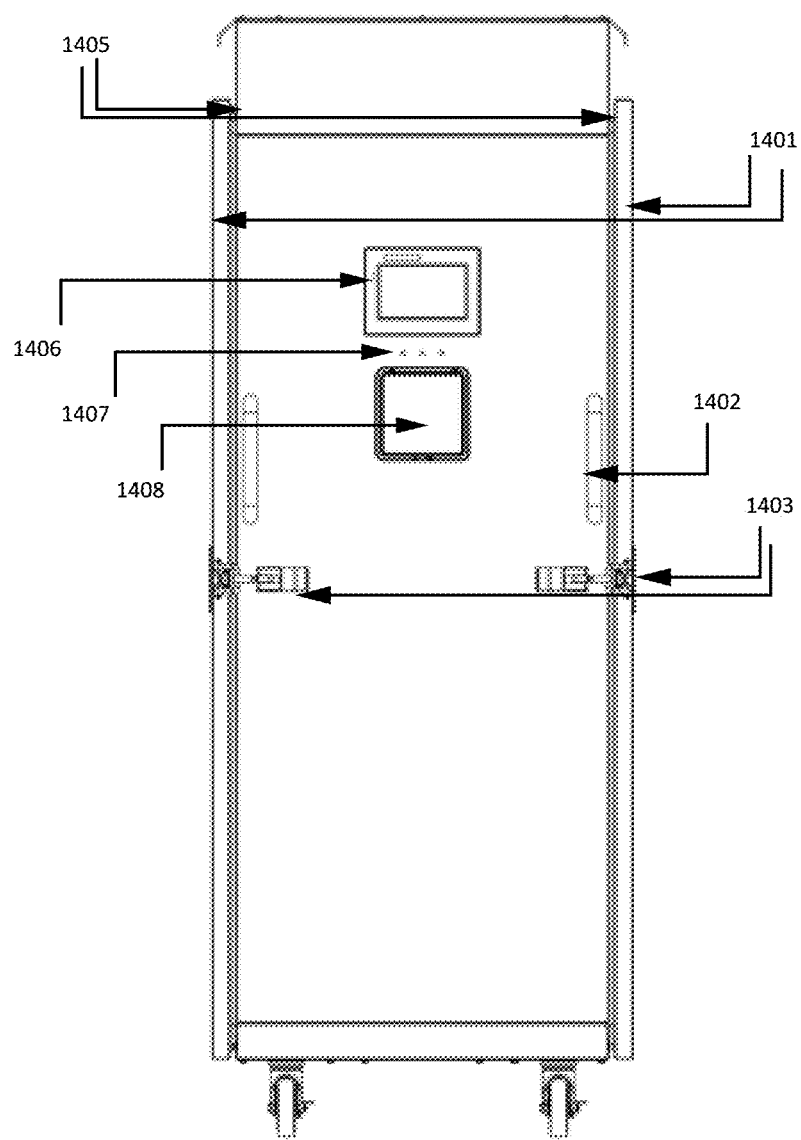
FIG. 14 illustrates a side view of a multiple access door embodiment whereby doors are located on opposite sides of the cabinet.

FIG. 14 illustrates a side view of a multiple access door embodiment whereby doors 1401 are located on opposite sides of the cabinet with a steering handle 1402 on each side, each door with a manual lock 1403. A further safety door embodiment provides an automated lock 1405 on any access door 1401. The front-facing status embodiment allows for complete machine status to be visible from the front plane 1409 containing a computer screen HMI 1406, status indicator lights 1407 and viewing window 1408 and manual door locks 1403.

Figure 15:
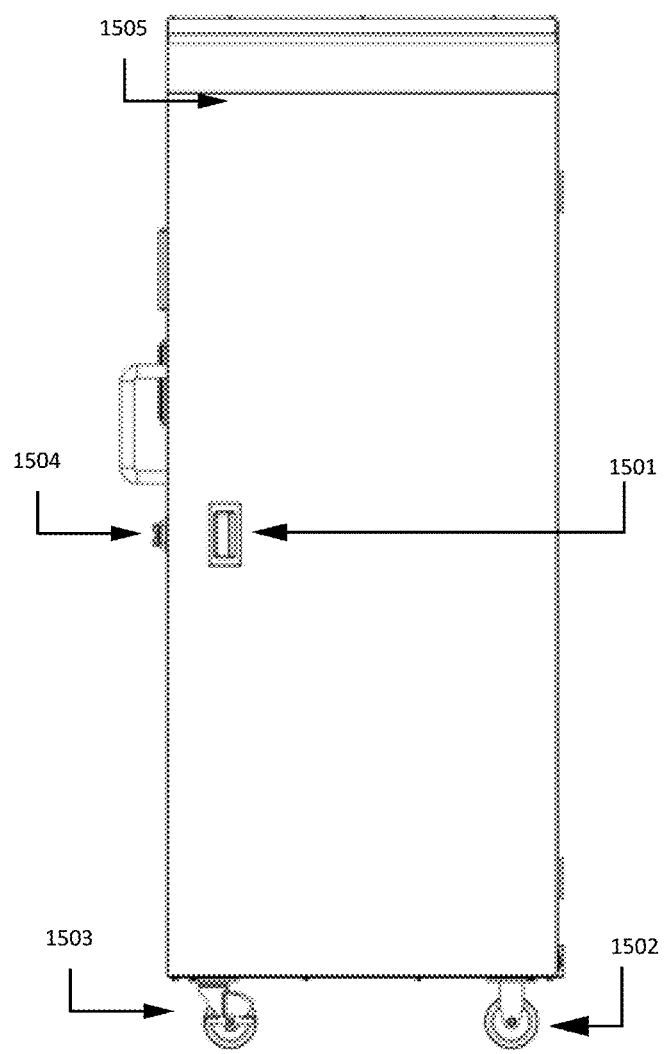
FIG. 15 shows an embodiment including a door with pull handle.

FIG. 15 shows an embodiment including a door with pull handle 1501, manual door lock 1504, automated door lock 1505, fixed wheel 1502 and steerable, lockable wheel 1503.

Figure 16:
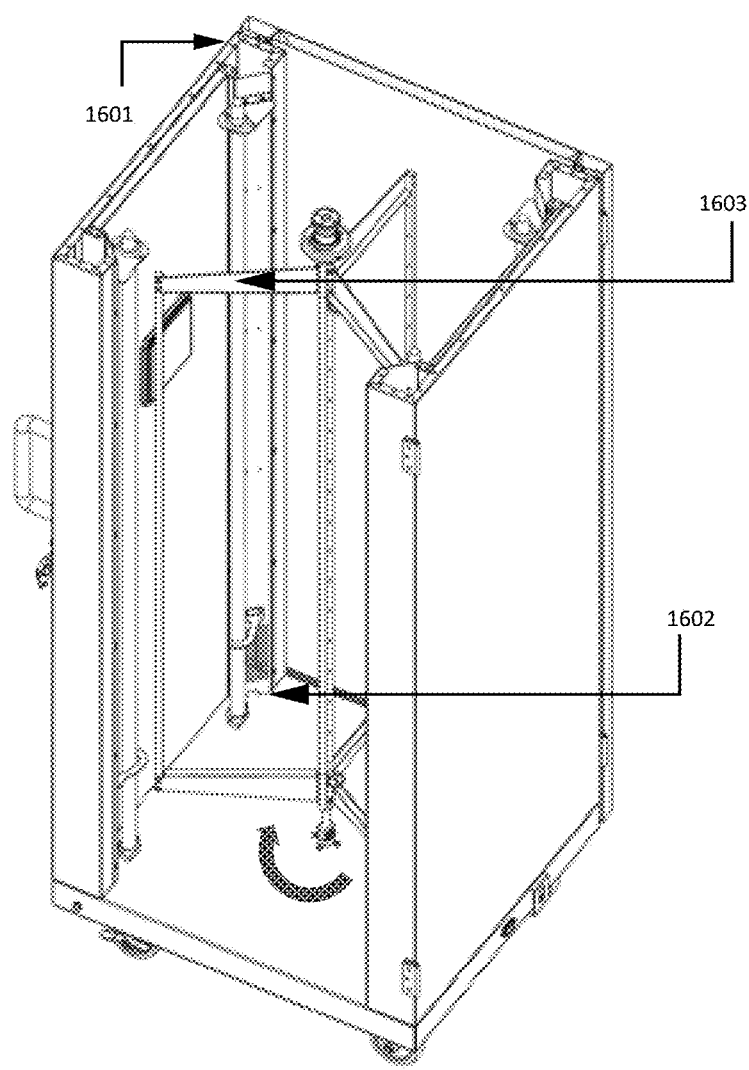
FIG. 16 illustrates a perspective cut away view of a four-corner embodiment where the cabinet's structural frame is also an air duct.

FIG. 16 illustrates a perspective cut away view of a four-corner embodiment where the cabinet's structural frame is also an air duct at each corner 1601 where the duct extends as part of the cabinet frame the full length of the interior cabinet space, providing controlled air flow from top of duct 1601 to bottom of duct 1602. As the carrousel 1603 rotates, the air flow is moved vertically from bottom to top.

Figure 17:
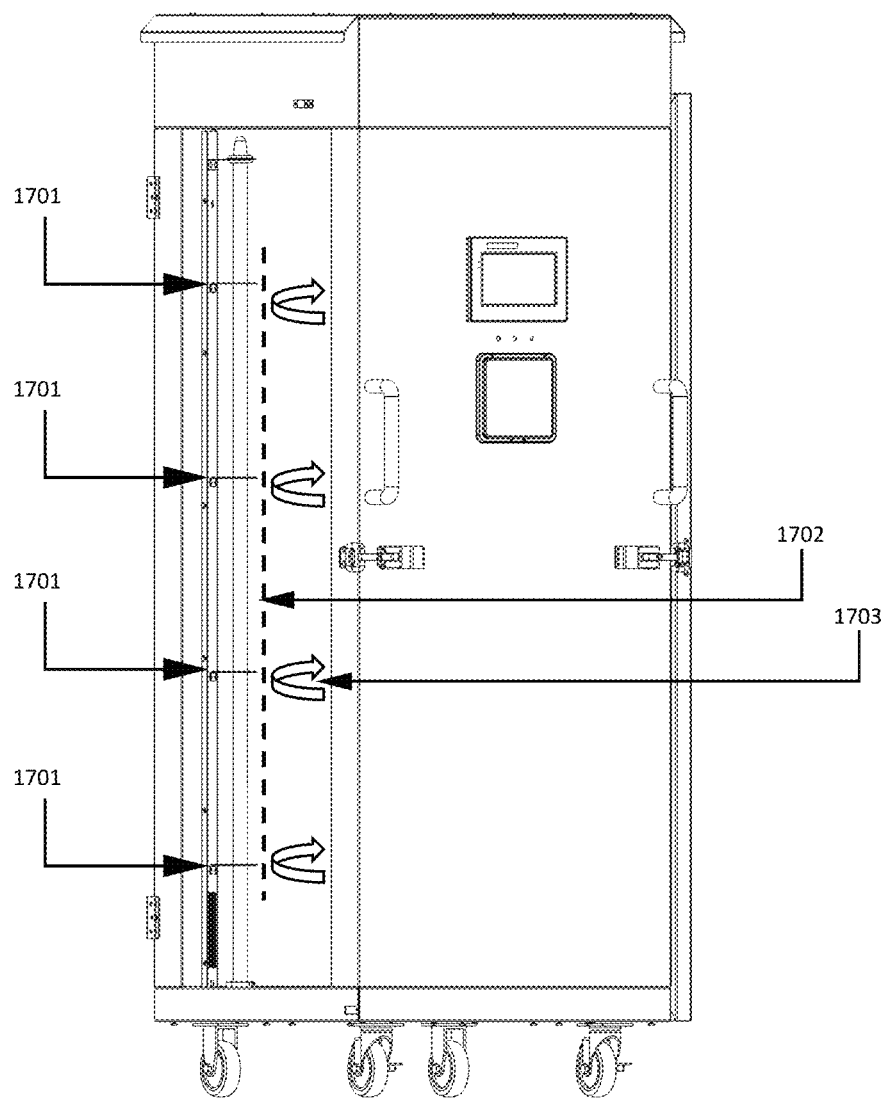
FIG. 17 illustrates an embodiment of the cabinet's internal space using item physical guides.

FIG. 17 illustrates an embodiment of the cabinet's internal space using item physical guides. As the framework carrousel moves at its center point 360° within carrousel movement area 1703 items contained within the carrousel could potentially shift outside of intended movement range 1702 whereby all or a portion of any item could extend beyond the carrousel movement area 1703 and if so, item physical guide points 1701 are positioned to protrude and nudge the item toward carrousel movement area 1703 and prevent the item from leaving the carrousel movement area 1703 where the item would be prevented from receiving or would prevent other items from receiving full treatment by chosen disinfection methods. The item physical guides provide a new and improved item disinfection system and method which has built-in physical guide material on the interior of the enclosure or door assembly whereby any item that becomes misaligned with its intended position as it rotates is nudged toward its original intended position so that it remains in place for exposure as well as it does not affect any other item or the cabinet's mechanisms. Alternatively, the item can be moved upon a conveyor or carriage and a similar physical guide can be positioned to assure the item remains in its intended position throughout the treatment cycle.

One embodiment provides a new and improved item disinfection system and method which provides the operator with an operator viewing window that is safety glass and UV-C resistant thereby allowing the operator to observe the interior of the cabinet at all times.

One embodiment provides a new and improved item disinfection system and method which provides the operator with an operator screen that allows the selection of cycle modes, settings, timings, as well as system status communication methods whereby the operator can see the current status, error messages, instructions and more.

One embodiment provides a new and improved item disinfection system and method which has lights and indicators on both operating sides of the cabinet whereby the lights and screens communicate the machine status (e.g. "Dirty/Ready for Loading", "In-Use", "Clean/Ready for Unloading", etc.) using colors and words to easily convey to the operator a status.

One embodiment provides a new and improved item disinfection system and method which features a full system test cycle upon powering up the cabinet. A test cycle tests all disinfection subsystems and sensors for proper working order and asks the operator to confirm a success. This test cycle provides confidence that all subsequent activity is being performed properly.

One embodiment provides a new and improved item disinfection system and method which includes dynamic control software that contains actions and decisions using sensor inputs to perform the selected disinfection treatment cycle.

One embodiment provides a new and improved item disinfection system and method which has a smooth exterior surface on all sides with no exposed wires or cords or protruding parts that could be caught during operation or transportation of the cabinet.

One embodiment provides a new and improved item disinfection system and method which requires only a single 120v 15a power connection to accomplish all operations and is easily powered by external power generators or a battery pack.

One embodiment provides a new and improved item disinfection system and method which enables matching the disinfection treatment plan to the items (and their materials) requiring disinfection. A disinfection treatment plan is based upon [contaminant×materials×disinfection method×duration]. The ability to include (or exclude) a disinfection method based upon a material match (or conflict) is part of this embodiment.

One embodiment provides a new and improved item disinfection system and method which provides operating software controls that assure a disciplined/metered treatment efficacy for the varied items and materials and contaminants requiring disinfection, operate and communicate system and cycle status.

One embodiment provides a new and improved item disinfection system and method which can be self-operated by the institution, requiring no 3rd party expense or dependency.

One embodiment provides a new and improved item disinfection system and method which is a "closed system" whereby no air or vapor may be evacuated outside the enclosure for any purpose during or following the operation of the cabinet. The system is self-contained and inert at the end of any cycle whereby the enclosure, items, contaminants, and disinfection materials used in the treatment cycle do not affect the cabinet's operator or item's user or the cabinet's operating environment whereby additional precautions may be taken post-treatment or post-cycle.

One embodiment provides a new and improved item disinfection system and method which provides multiple disinfection methods and item manipulation whereby the cabinet maintains a sound level of 85 decibels or less and cannot be detected from outside a sealed operating area.

One embodiment provides a new and improved item disinfection system and method which allows the operator to place and remove items within the cabinet without having to step into the enclosure or reach or bend or stoop in a manner that causes physical strain or long-term fatigue or injury. A further object is to allow 100% access to the entire enclosure from any door whereby there are no physical panels or barriers between any portion of the interior workspace and the outside when the door is opened (this means the doors can be 100% of the side of the enclosure).

One embodiment provides a new and improved item disinfection system and method which allows an item to fall from its original mounted position inside the enclosure to the bottom of the enclosure whereby the system can continue to operate without damaging the item else the system will stop operating. A further object is to have no moving parts, technology, or any component at the bottom of the enclosure whereby items or fluids could interfere with a disinfection cycle or damage the enclosure or its components.

One embodiment provides a new and improved item disinfection system and method which is susceptible to a low cost of manufacture with regard to both materials and labor, and which accordingly is then susceptible to low prices of sale to the consuming industry, thereby making such cabinet economically available to those in the industry.

One embodiment provides a new and improved item disinfection system and method which provides all of the advantages of the prior art, while simultaneously overcoming some of the disadvantages normally associated therewith.

CONCLUSION

Although the subject matter has been described in terms of certain embodiments, other embodiments that may or may not provide various features and aspects set forth herein shall be understood to be contemplated by this disclosure. The specific embodiments described above are disclosed as examples only, and the scope of the patented subject matter is defined by the claims that follow. In the claims, the terms "based upon" and "based on" shall include situations in which a factor is taken into account directly and/or indirectly, and possibly in conjunction with other factors, in producing a result or effect. In the claims, a portion shall include greater than none and up to the whole of a thing.

What is claimed is:

1. A disinfection cabinet comprising:
   a transportable cabinet frame having a base, at least one bounding wall positioned substantially perpendicular to the base, and a top coupled with the at least one bounding wall;
   at least one rotating framework for holding and presenting items for disinfection within an interior of the cabinet, the at least one rotating framework including a first member configured to rotate about an axis and at least one second member coupled to the first member and positioned outward from the first member, the at least one second member having at least one attachment point, the at least one attachment point configured to selectively couple with an item holder to position an item to be disinfected at least partially toward the first member; and
   at least one light source positioned within the interior of the cabinet, the at least one light source configured to facilitate disinfection of an item to be disinfected.

2. The cabinet of claim 1, further comprising:
   at least one heat source configured to heat the interior of the cabinet; and
   at least one vapor delivery source configured to deliver a disinfecting vapor within the interior of cabinet.

3. The cabinet of claim 2, wherein the at least one vapor delivery source is configured to regulate humidity and chemical saturation level within the cabinet.

4. The cabinet of claim 1, further comprising:
   at least two access doors mounted to the cabinet frame and providing access to the interior of the cabinet through two access door openings, wherein each of the access door openings is positioned on an opposite side of the cabinet frame.

5. The cabinet of claim 1, further comprising:
   a fan coupled with the cabinet frame and configured to circulate air within the interior of the cabinet.

6. The cabinet of claim 1, wherein an air source is configured to provide a supply of air to or remove air from the interior of the cabinet.

7. The cabinet of claim 1, further comprising a control system configured to control and regulate application of multiple disinfection methods in accordance with a customizable treatment plan.

8. The cabinet of claim 7, wherein the customizable treatment plan is based upon a type or composition of the item.

9. The cabinet of claim 1, further comprising:
   for at least one of the at least one rotating framework, at least one guide feature extending substantially vertically for at least a majority of a height of the at least one rotating framework, the at least one guide feature extending along substantially parallel to the axis and configured to nudge an item to be disinfected supported by the item holder into intended positions within a predefined circumference around the axis.

10. The cabinet of claim 1, wherein the item holder is coupled to the at least one second member with a centerline of the item holder being angled between an intersection of a first plane tangent to a circumference of rotation of the at least one second member and a second plane extending along the axis and the at least one second member.

11. The cabinet of claim 1, further comprising a drive mechanism configured to rotate the at least one rotating framework, wherein the drive mechanism is configured to permit slippage of rotation of the at least one rotating framework in case of blockage or manual movement of the at least one rotating framework during loading or unloading.

12. A method for disinfecting items comprising:
    enabling an opening of a first access door providing access to an interior of a transportable disinfection cabinet through a first opening in the cabinet;
    receiving a loading, through the first opening, of an item at least partially onto an item holder, the item holder being coupled to an attachment point on a rotating framework within the interior of the cabinet, the framework including a first member configured to rotate about an axis and at least one second member, the at least one second member coupled to the first member and positioned outward from the first member, wherein the item at least partially on the item holder is positioned at least partially toward the first member with the item holder coupled to the attachment point;
    enabling a closing of the first access door after loading the item;
    performing a disinfection process on contents of the cabinet, wherein the disinfection process comprises:
       rotating the framework about the axis within the interior of the cabinet, and
       exposing the item to a light source positioned within the interior of the cabinet, the light source configured to facilitate a disinfection of the item;
    in response to an indication that the disinfection process is complete, enabling an opening of a second access door providing internal access to the interior of the cabinet through a second opening in the cabinet positioned on an opposite side of the cabinet from the first opening; and enabling a removing of the item from the framework through the second opening.

13. The method of claim 12, wherein the disinfection process further comprises:

exposing the item to air movement and circulation within the interior of the cabinet;

operating a heat source configured to heat the interior of the cabinet; and operating a vapor delivery source configured to deliver a disinfecting vapor to the interior of the cabinet.

14. The method of claim 13, wherein the disinfecting vapor comprises water vapor, and wherein the water vapor raises a humidity level in the interior of the cabinet.

15. The method of claim 14, wherein the disinfection process is driven by a control system configured to control and regulate application of multiple disinfection mechanisms in accordance with a customizable treatment plan.

16. The method of claim 15, wherein the control system receives data from one or more sensors within the cabinet to sense: motion of the item within the interior of the cabinet, and operation of one or more disinfection methods, wherein the control system is configured to control the customizable treatment plan in response to data received from the one or more sensors.

17. The method of claim 15, wherein the customizable treatment plan is based upon a type or composition of the item.

18. The method of claim 12, further comprising:

contacting, by at least one guide feature positioned within the interior of the cabinet, the item as the framework rotates, the at least one guide feature configured to nudge the item into an intended position within a predefined circumference around the axis as the framework rotates.

19. The method of claim 12, wherein the item holder is attached to the at least one second member with a centerline that is angled between an intersection of a first plane tangent to a circumference of rotation of the at least one second member and a second plane extending along the axis and the at least one second member.

20. The method of claim 12, wherein the item comprises personal protective equipment.

* * * * *

UNITED STATES PATENT AND TRADEMARK OFFICE
CERTIFICATE OF CORRECTION

| | | |
|---|---|---|
| PATENT NO. | : 12,263,260 B1 | Page 1 of 1 |
| APPLICATION NO. | : 17/374890 | |
| DATED | : April 1, 2025 | |
| INVENTOR(S) | : Whitaker | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 859 days.

Signed and Sealed this
Sixth Day of January, 2026

John A. Squires
*Director of the United States Patent and Trademark Office*